(12) United States Patent
Coyne et al.

(10) Patent No.: US 11,771,574 B2
(45) Date of Patent: Oct. 3, 2023

(54) ESOPHAGEAL STENT INCLUDING A VALVE MEMBER

(71) Applicant: BOSTON SCIENTIFIC SCIMED, INC., Maple Grove, MN (US)

(72) Inventors: Martin Coyne, Galway (IE); Niall Feeney, Galway (IE); James Byrne, Galway (IE); Harshad Holehonnur, Galway (IE); Jonathan Dolan, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 309 days.

(21) Appl. No.: 17/123,449

(22) Filed: Dec. 16, 2020

(65) Prior Publication Data

US 2021/0186723 A1    Jun. 24, 2021

Related U.S. Application Data

(63) Continuation of application No. 16/176,451, filed on Oct. 31, 2018, now Pat. No. 10,888,444.

(Continued)

(51) Int. Cl.
*A61F 2/90* (2013.01)
*B29D 23/00* (2006.01)
(Continued)

(52) U.S. Cl.
CPC ............... *A61F 2/90* (2013.01); *A61F 2/04* (2013.01); *A61F 2/2412* (2013.01);
(Continued)

(58) Field of Classification Search
CPC .. A61F 2/90; A61F 2/04; A61F 2/2412; A61F 2/2418; A61F 2210/0076;
(Continued)

(56) References Cited

U.S. PATENT DOCUMENTS 5,064,435 A    11/1991  Porter
5,741,333 A    4/1998   Frid
(Continued)

FOREIGN PATENT DOCUMENTS

EP    1001718 A1    5/1998
EP    1065996 B1    12/2003
(Continued)

OTHER PUBLICATIONS

"AXIOS Stent: and Electrocautery Enhanced Delivery System," Boston Scientific Corporation, 4 pages, Dec. 2015.
(Continued)

*Primary Examiner* — Suzette J Gherbi
(74) *Attorney, Agent, or Firm* — Seager, Tufte & Wickhem, LLP

(57) ABSTRACT

An example medical device is disclosed. An example medical device includes an expandable stent. The stent includes a tubular scaffold formed of one or more interwoven filament. The tubular scaffold includes an inner surface and a flexible valve extending radially inward from the inner surface of the scaffold. Further, the valve is configured to shift between a closed configuration and an open configuration and the one or more filaments of the scaffold bias the valve to the closed configuration while in a nominally deployed state.

20 Claims, 19 Drawing Sheets

Related U.S. Application Data

(60) Provisional application No. 62/579,990, filed on Nov. 1, 2017.

(51) Int. Cl.
  *A61F 2/24* (2006.01)
  *A61F 2/04* (2013.01)
  A61L 27/36 (2006.01)

(52) U.S. Cl.
  CPC ............ *A61F 2/2418* (2013.01); *B29D 23/00* (2013.01); *A61F 2002/044* (2013.01); *A61F 2210/0076* (2013.01); *A61F 2230/0008* (2013.01); *A61F 2240/001* (2013.01); *A61F 2250/0039* (2013.01); *A61F 2250/0069* (2013.01); *A61L 27/3679* (2013.01)

(58) Field of Classification Search
  CPC ........ A61F 2230/0008; A61F 2240/001; A61F 2250/0039; A61F 2250/0069
  See application file for complete search history.

(56) References Cited

U.S. PATENT DOCUMENTS

| | | |
|---|---|---|
| 5,849,037 A | 12/1998 | Frid |
| 5,888,201 A | 3/1999 | Stinson et al. |
| 5,980,533 A | 11/1999 | Holman |
| 6,120,522 A | 9/2000 | Vrba et al. |
| 6,240,978 B1 | 6/2001 | Gianotti |
| 6,264,689 B1 | 7/2001 | Colgan et al. |
| 6,295,714 B1 | 10/2001 | Roychowdhury et al. |
| 6,302,917 B1 | 10/2001 | Dua et al. |
| 6,423,084 B1 | 7/2002 | St. Germain |
| 6,468,303 B1 | 10/2002 | Amplatz et al. |
| 6,558,429 B2 | 5/2003 | Taylor |
| 6,620,122 B2 | 9/2003 | Stinson et al. |
| 6,626,939 B1 | 9/2003 | Burnside et al. |
| 6,652,577 B2 | 11/2003 | Gianotti |
| 6,792,979 B2 | 9/2004 | Konya et al. |
| 6,997,945 B2 | 2/2006 | St. Germain |
| 7,001,423 B2 | 2/2006 | Euteneuer et al. |
| 7,018,401 B1 | 3/2006 | Hyodoh et al. |
| 7,048,014 B2 | 5/2006 | Hyodoh et al. |
| 7,160,323 B2 | 1/2007 | Pulnev et al. |
| 7,175,655 B1 | 2/2007 | Molaei |
| 7,311,031 B2 | 12/2007 | McCullagh et al. |
| 7,331,990 B2 | 2/2008 | Gianotti |
| 7,419,502 B2 | 9/2008 | Pulnev et al. |
| 7,419,503 B2 | 9/2008 | Pulnev et al. |
| 7,462,192 B2 | 12/2008 | Norton et al. |
| 7,476,256 B2 | 1/2009 | Meade et al. |
| 7,637,938 B2 | 12/2009 | Brown et al. |
| 7,670,367 B1 | 3/2010 | Chouinard et al. |
| 7,670,369 B2 | 3/2010 | Schaeffer |
| 7,736,386 B2 | 6/2010 | Pulnev et al. |
| 7,763,011 B2 | 7/2010 | Ortiz et al. |
| 7,763,068 B2 | 7/2010 | Pulnev et al. |
| 7,815,591 B2 | 10/2010 | Levine et al. |
| 7,857,844 B2 | 12/2010 | Norton et al. |
| 7,927,366 B2 | 4/2011 | Pulnev et al. |
| 8,092,512 B2 | 1/2012 | Rudnick et al. |
| 8,105,392 B2 | 1/2012 | Durgin |
| 8,109,992 B2 | 2/2012 | Pulnev et al. |
| 8,114,147 B2 | 2/2012 | Wood et al. |
| 8,151,682 B2 | 4/2012 | Lilburn et al. |
| 8,197,528 B2 | 6/2012 | Colgan et al. |
| 8,211,186 B2 | 7/2012 | Belhe et al. |
| 8,221,505 B2 | 7/2012 | Skerven |
| 8,262,719 B2 | 9/2012 | Erickson et al. |
| 8,357,193 B2 | 1/2013 | Phan et al. |
| 8,414,635 B2 | 4/2013 | Hyodoh et al. |
| 8,425,539 B2 | 4/2013 | Binmoeller et al. |
| 8,454,632 B2 | 6/2013 | Binmoeller et al. |
| 8,491,647 B2 | 7/2013 | Colgan et al. |
| 8,597,366 B2 | 12/2013 | Shank |
| 8,623,071 B2 | 1/2014 | Lundkvist et al. |
| 8,647,381 B2 | 2/2014 | Essinger et al. |
| 8,677,874 B2 | 3/2014 | Lilburn et al. |
| 9,044,300 B2 | 6/2015 | Belhe et al. |
| 9,211,182 B2 | 12/2015 | Errico et al. |
| 9,439,791 B2 | 9/2016 | Vong et al. |
| 9,526,648 B2 | 12/2016 | Sharma |
| 9,566,182 B2 | 2/2017 | Durgin |
| 10,888,444 B2 * | 1/2021 | Coyne .................. A61F 2/04 |
| 11,517,430 B1 * | 12/2022 | Palmaz .................. A61L 27/34 |
| 2002/0107565 A1 | 8/2002 | Greenhalgh |
| 2003/0032967 A1 | 2/2003 | Park et al. |
| 2003/0055492 A1 * | 3/2003 | Shaolian .............. A61F 2/2403 |
| | | 623/2.18 |
| 2003/0069646 A1 | 4/2003 | Stinson |
| 2003/0083734 A1 | 5/2003 | Friedrich et al. |
| 2004/0093058 A1 | 5/2004 | Cottone et al. |
| 2007/0112415 A1 | 5/2007 | Bartlett |
| 2007/0112437 A1 | 5/2007 | Shank |
| 2007/0179590 A1 | 8/2007 | Lu et al. |
| 2008/0243151 A1 | 10/2008 | Binmoeller et al. |
| 2009/0138071 A1 | 5/2009 | Cheng et al. |
| 2009/0248171 A1 | 10/2009 | Levine et al. |
| 2010/0049306 A1 | 2/2010 | House et al. |
| 2010/0114327 A1 | 5/2010 | Sobrino-Serrano |
| 2010/0305590 A1 | 12/2010 | Holmes et al. |
| 2011/0137399 A1 * | 6/2011 | Chomas ............ A61M 25/0075 |
| | | 623/1.12 |
| 2011/0190905 A1 | 8/2011 | Behan |
| 2012/0158118 A1 * | 6/2012 | Rowe .................. A61F 2/2433 |
| | | 623/1.11 |
| 2013/0030351 A1 | 1/2013 | Belhe et al. |
| 2013/0053950 A1 | 2/2013 | Rowe et al. |
| 2013/0289711 A1 * | 10/2013 | Liddy .................. A61F 2/04 |
| | | 427/2.25 |
| 2014/0046424 A1 * | 2/2014 | Perkins ................. A61F 2/95 |
| | | 623/1.11 |
| 2014/0081416 A1 | 3/2014 | Clerc et al. |
| 2014/0350694 A1 | 11/2014 | Behan |
| 2014/0364959 A1 | 12/2014 | Attar et al. |
| 2016/0081832 A1 | 3/2016 | Hingston et al. |
| 2017/0056150 A1 | 3/2017 | Stinson |
| 2017/0252144 A1 | 9/2017 | Hannon et al. |
| 2020/0113684 A1 * | 4/2020 | Tabor .................. A61F 2/07 |
| 2022/0273471 A1 * | 9/2022 | Folan .................. A61F 2/88 |

FOREIGN PATENT DOCUMENTS

| | | | |
|---|---|---|---|
| EP | 1229864 B1 | 4/2005 | |
| EP | 975279 B1 | 5/2007 | |
| EP | 1560544 B1 | 1/2008 | |
| EP | 2273942 A1 | 11/2009 | |
| EP | 2276390 A1 | 11/2009 | |
| EP | 2194887 A1 | 6/2010 | |
| EP | 1598032 B1 | 3/2011 | |
| EP | 1755462 A1 | 3/2011 | |
| EP | 2389877 A2 | 11/2011 | |
| EP | 2391752 A2 | 12/2011 | |
| EP | 2407127 B1 | 1/2012 | |
| EP | 1833417 B1 | 2/2012 | |
| EP | 2434961 B1 | 1/2015 | |
| WO | 2008103572 A1 | 8/2008 | |

OTHER PUBLICATIONS

Blackwell, "What is the mean Lower Esophageal Sphincter Pressure in normal subjects?" Oeso Knowledge, 2 pages, May 1991.
Booth, "Vomiting Larry: a simulated vomiting system for assessing environmental contamination from projectile vomiting related to norovirus infection," Journal of Infection Prevention, 15(5): pp. 176-180, Sep. 2014.
Bowen, "Physiology of Vomiting," VIVO Pathophysiology, 4 pages, downloaded Aug. 11, 2017.
Cowgill et al., "Normal lower esophogeal sphincter pressure and length does not impact outcome after laparoscopic Nissen fundoplication," PubMed, 11(6): 2 pages, Jun. 2007. Abstract Only.

(56) References Cited

OTHER PUBLICATIONS

Dua et al., "Self-expanding metal esophageal stent with anti-reflux mechanism," GIE Journal, 53(6): 2 pages, May 2001. Abstract Only.
"Gastroesophageal Reflux Disease," National Cancer Institute, 2 pages, downloaded Aug. 11, 2017.
Hayden et al., "Fecal Incontinence: Etiology, Evaluation, and Treatment," Clinics in Colon and Rectal Surgery, 24(1): pp. 64-70, Mar. 2011.
Mashimo et al., "Physiology of esophageal motility," GI Motility online, 36 pages, May 16, 2006.
International Search Report and Written Opinion dated Feb. 13, 2019 for International Application No. PCT/US2018/058431.
"Polyimide Tubing: Dispelling The Myths," MicroLumen High Performance Medical Tubing, 8 pages, Downloaded Aug. 11, 2017.
Sajadi et al., "Artificial Urinary Sphincter Placement Treatment & Management," Medscape, 1 page, May 16, 2016.

* cited by examiner

ESOPHAGEAL STENT INCLUDING A VALVE MEMBER

CROSS-REFERENCE TO RELATED APPLICATIONS

This is a continuation of U.S. application Ser. No. 16/176,451, filed Oct. 31, 2018, which application claims priority under 35 U.S.C. § 119 to U.S. Provisional Application Ser. No. 62/579,990, filed Nov. 1, 2017, the entirety of which is incorporated herein by reference.

TECHNICAL FIELD

The present disclosure pertains to medical devices, methods for manufacturing medical devices, and uses thereof. More particularly, the present disclosure pertains to stents including a valve, such as an anti-reflux valve, and methods for manufacturing and using such stents.

BACKGROUND

The lower esophageal sphincter is a muscle located between the esophagus and the stomach. The sphincter normally functions as a one-way valve, allowing material (e.g., food) that travels downward through the esophagus to enter the stomach while preventing the backflow (reflux) of hydrochloric acid and other gastric contents into the esophagus. However, in some cases the lower esophageal sphincter does not close adequately, and therefore, permits stomach acid to reflux into the esophagus, causing heartburn. A weak or inoperable lower esophageal sphincter is a major cause of gastroesophageal reflux disease (GERD).

Therefore, a variety of intracorporeal medical devices have been developed to treat gastroesophageal disease caused by a malfunctioning lower esophageal sphincter. For example, elongated stents incorporating flexible valves have been developed to allow material (e.g., food) to travel through the esophagus and enter the stomach while also preventing stomach acid to reflux into the esophagus. However, there is an ongoing need to provide alternative configurations of and/or methods of forming stents including a two-way valve to treat gastroesophageal disease, as well as other medical conditions.

BRIEF SUMMARY

This disclosure provides design, material, manufacturing method, and use alternatives for medical devices. An example medical device includes an expandable stent. The stent includes a tubular scaffold formed of one or more interwoven filament. The tubular scaffold includes an inner surface and a flexible valve extending radially inward from the inner surface of the scaffold. Further, the valve is configured to shift between a closed configuration and an open configuration and the one or more filaments of the scaffold bias the valve to the closed configuration while in a nominally deployed state.

Alternatively or additionally to any of the embodiments above, wherein the valve shifts from the closed configuration to the open configuration due to a peristaltic force applied to the tubular scaffold.

Alternatively or additionally to any of the embodiments above, wherein the valve includes a valve opening extending therethrough, and wherein the valve opening is ovular-shaped in the open configuration.

Alternatively or additionally to any of the embodiments above, wherein the tubular scaffold includes a first tapered region and a second tapered region, and wherein the valve is positioned between the first tapered region and the second tapered region.

Alternatively or additionally to any of the embodiments above, wherein the first tapered region is configured to funnel material toward the valve.

Alternatively or additionally to any of the embodiments above, wherein the one or more filaments of the scaffold are configured to radially expand to shift the valve from the closed configuration to the open configuration when subjected to a radial expansion force of 0.800 $N/cm^2$ or greater.

Alternatively or additionally to any of the embodiments above, further comprising a coating disposed along the one or more filaments, and wherein the valve is formed from a portion of the coating.

Alternatively or additionally to any of the embodiments above, the valve is a two-way valve configured to permit material to pass through the valve in a first direction and a second direction, and wherein the first direction is opposite the second direction.

An example method of manufacturing a stent includes forming a tubular scaffold, wherein the tubular scaffold includes a first end, a second end and a narrowed region positioned between the first end and the second end. The tubular scaffold is positioned on a coating mandrel such that the coating mandrel radially expands the narrowed region such that the tubular scaffold is spaced away from the coating mandrel at the narrowed region. A coating is applied to the tubular scaffold while the tubular scaffold is positioned on the coating mandrel. Applying the coating to the tubular scaffold includes forming a valve within the narrowed region of the tubular scaffold. Thereafter, the tubular scaffold is removed from the coating mandrel and the tubular scaffold radially collapses at the narrowed region to bias the valve in a closed configuration after being removed from the coating mandrel.

Alternatively or additionally to any of the embodiments above, wherein forming the tubular scaffold comprises braiding at least two or more stent filaments together.

Alternatively or additionally to any of the embodiments above, wherein forming the tubular scaffold further comprises positioning the tubular scaffold on a shaping mandrel, and wherein the shaping mandrel is configured to radially pinch the one or more filaments to create the narrowed region.

Alternatively or additionally to any of the embodiments above, wherein forming the tubular scaffold further comprises heat treating the tubular scaffold while the tubular scaffold is positioned on the shaping mandrel.

Alternatively or additionally to any of the embodiments above, wherein applying the coating to the tubular scaffold further includes spraying the coating on the tubular scaffold.

Alternatively or additionally to any of the embodiments above, wherein the valve has an ovular-shaped opening in an open configuration.

Another example expandable stent includes a braided tubular scaffold formed of a plurality of interwoven filaments. The tubular scaffold includes a first end, a second end and a lumen extending therethrough. The tubular scaffold further includes a narrowed region positioned between the first end and the second end. A flexible valve is positioned within the lumen at the narrowed region. The plurality of interwoven filaments apply a radially compressive force on the valve to bias the valve to a closed configuration while the stent is in a nominally deployed state.

Alternatively or additionally to any of the embodiments above, wherein the radially compressive force is less than or equal to 0.800 N/cm$^2$.

Alternatively or additionally to any of the embodiments above, wherein the narrowed region includes a first diameter while in the nominally deployed state, and wherein the narrowed region is configured to radially expand to open the valve when subjected to a radially expanding force of 0.800 N/cm$^2$ or greater.

Alternatively or additionally to any of the embodiments above, wherein the valve shifts from the closed configuration to an open configuration due to a peristaltic force applied to the plurality of interwoven filaments.

Alternatively or additionally to any of the embodiments above, wherein the valve includes a valve opening extending therethrough, and wherein the valve opening is ovular-shaped in the open configuration.

Alternatively or additionally to any of the embodiments above, further comprising a coating disposed along the plurality of filaments, and wherein the valve is formed from a portion of the coating.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
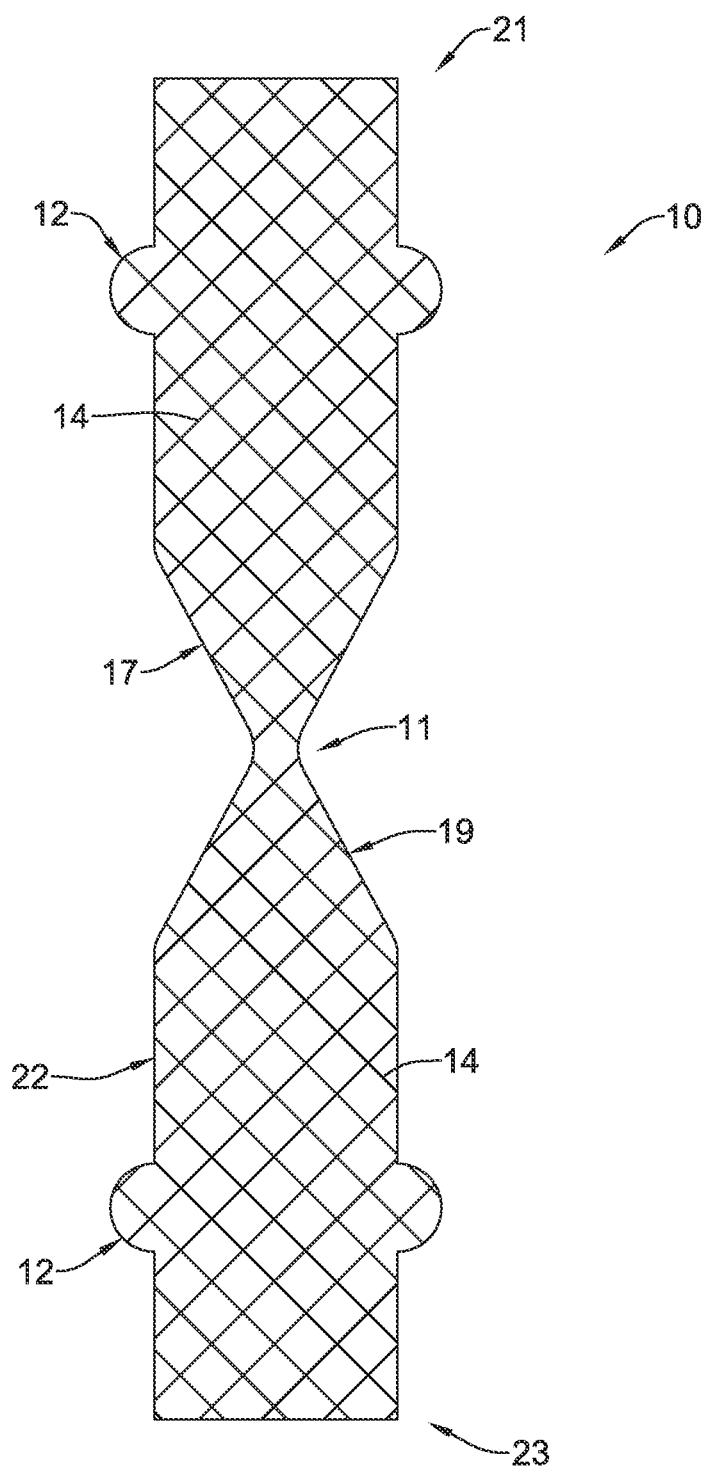
FIG. 1 is an example stent.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

Gastroesophageal reflux disease (GERD) is a medical condition whereby stomach acids enter the lower portion of the esophagus because the lower esophageal sphincter (positioned at the entrance of the stomach) fails to close properly. In some instances, the lower esophageal sphincter's inability to close is due to disease or general atrophy. When left open, the sphincter may permit reflux of stomach acids into the esophagus, causing severe heartburn and potentially contributing to the onset of other diseases.

One method of treating GERD is to place an anti-reflux stent into the entrance of the stomach. An anti-reflux stent may include an expandable two-way valve which allows food and liquid to enter the stomach but limits liquids (stomach acids) from passing back through the valve under normal digestive conditions (e.g., the valve may permit liquids to pass back through the valve during periods then the stomach contracts to permit vomiting). In general, there is an ongoing need for an anti-reflux stent to provide a smooth lumen opening into the stomach while limiting stomach acids from passing back through the valve and into the esophagus.

FIG. 1 shows an example stent 10. Stent 10 may include a tubular scaffold 22 having a first end, which may extend to the first end of the stent 10, a second end, which may extend to the second end of the stent 10, and a lumen extending therethrough. The tubular scaffold 22 may be configured to provide the support structure for stent 10. The tubular scaffold 22 may be formed of one or more stent filaments 14, or a plurality of stent filaments 14. Filaments 14 may extend longitudinally along stent 10. In some instances, filaments 14 may extend longitudinally along stent 10 in a helical fashion. While FIG. 1 shows filaments 14 extending along the entire length of stent 10 between first and second ends of stent 10, in other examples, the filaments 14 may extend only along a portion of the length of stent 10.

Additionally, FIG. 1 shows example stent 10 including one or more enlarged portions (e.g., flanges) 12 proximate the first end 21 and second end 23 of the stent 10. In some instances, enlarged portions 12 may be defined as an increase in the outer diameter, the inner diameter or both the inner and outer diameter of stent 10 relative to a medial region of the stent 10. The enlarged portions 12 may be beneficial to anchor the stent within the esophagus and/or the opening to the stomach. Additionally, as will be described in greater detail below, FIG. 1 illustrates stent 10 including a first tapered portion 17, a second tapered portion 19 and a narrowed region 11 positioned between the first tapered portion 17 and the second tapered portion 19. First tapered portion 17 may taper toward the narrowed region (i.e., neck) 11 from a larger diameter to a smaller diameter, while second tapered portion 19 may taper toward the narrowed region (i.e., neck) 11 from a larger diameter to a smaller diameter.

In some instances, stent 10 may be a self-expanding stent. Self-expanding stent examples may include stents having one or more interwoven filaments 14 to form a tubular scaffold 22, having openings defined between adjacent filaments 14. For example, stent filaments 14 may be wires braided, knitted or otherwise interwoven to form the tubular scaffold 22. Openings or interstices through the wall of the tubular scaffold 22 may be defined between adjacent stent filaments 14. Alternatively, tubular scaffold 22 of stent 10 may be a monolithic structure formed from a cylindrical tubular member, such as a single, cylindrical tubular laser-cut Nitinol tubular member, in which the remaining portions of the tubular member form the stent filaments 14 with openings defined therebetween.

Stent 10, or components thereof, (including tubular scaffold 22 and/or stent filaments 14) disclosed herein may be constructed from a variety of materials. For example, stent 10 (e.g., self-expanding or balloon expandable), or components thereof, may be constructed from a metal (e.g., Nitinol). In other instances, stent 10 or components thereof may be constructed from a polymeric material (e.g., PET). In yet other instances, stent 10, or components thereof, may be constructed from a combination of metallic and polymeric materials. Additionally, stent 10, or components thereof, may include a bioabsorbable and/or biodegradable material.

Figure 2:
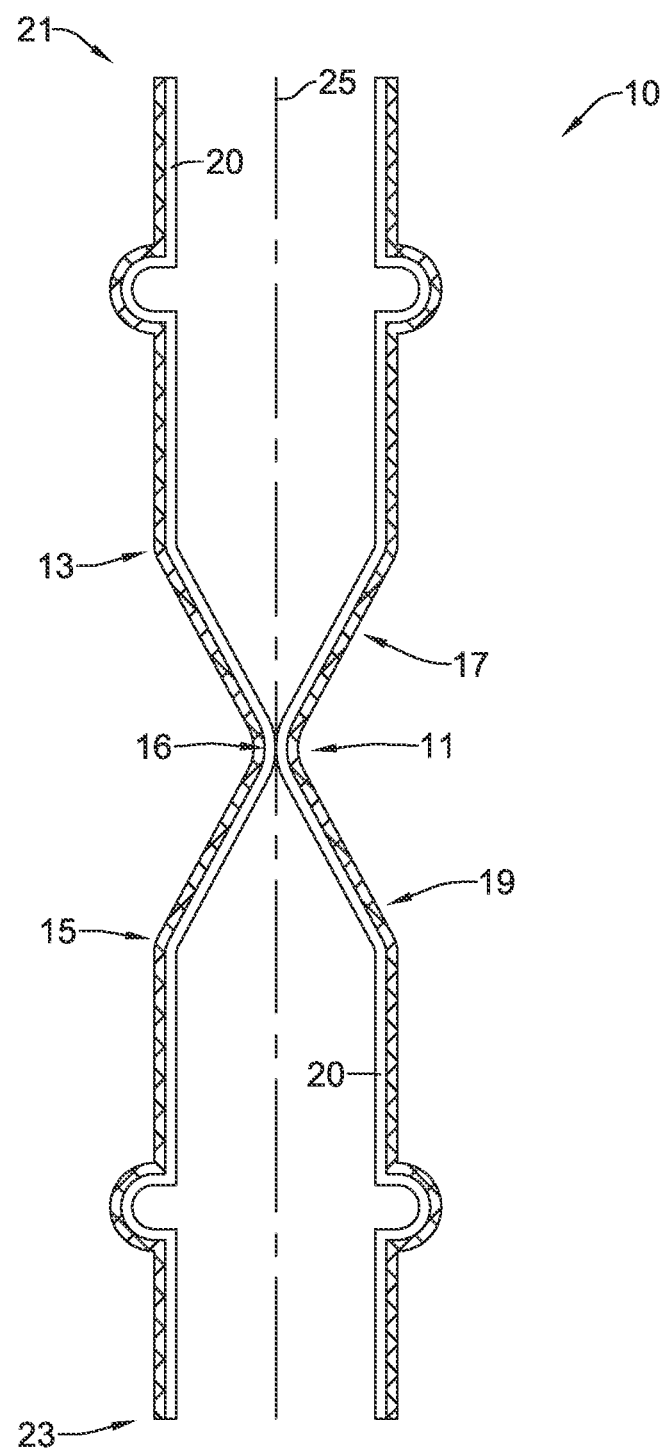
FIG. 2 is a cross-sectional view of the stent of FIG. 1 including a valve.

Additionally, stent 10 may include one or more coating layers disposed on tubular scaffold 22, such as positioned on and/or adjacent to the inner surface and/or outer surface thereof. The coating layer may be positioned on a portion of filaments 14 forming tubular scaffold 22 and extend across openings or cells between adjacent filaments 14. For example, FIG. 2 shows stent 10 including a coating layer 20 disposed along the inner surface of tubular scaffold 22. In some instances, coating layer 20 may be an elastomeric or non-elastomeric material. For example, coating layer 20 may be a polymeric material, such as silicone, polyurethane, or the like. Further, the coating layer 20 may span the spaces (e.g., openings, cells, interstices) in the wall of tubular scaffold 22 defined between adjacent filaments 14. For example, the coating layer 20 may extend along and cover the inner surface and/or outer surface of tubular scaffold 22 such that the coating layer 20 spans one or more of spaces (e.g., openings, cells, interstices) between filaments 14 in the wall of tubular scaffold 22.

As described above, stent 10 may have a first end 21 and a second end 23. When positioned in a body lumen (e.g., esophagus) first end 21 may be defined as the proximal end of stent 10 and oriented as the end of stent 10 closest to a patient's mouth and second end 23 may be defined as the distal end of stent 10 and oriented as the end of stent 10 closest to a patient's stomach. In some examples, a first end region of stent 10 extending proximal of a proximal most flange 12 may be longer than a second end region of stent 10 extending distal of a distal most flange 12. The additional length of first end region may extend into and cover the lower esophagus in the event a small amount of stomach acid were to leak through the valve 16 (shown in FIG. 2).

As shown in FIG. 2, coating layer 20 may extend along the length of tubular scaffold 22 from first end 21 to second end 23. In other words, in some instances coating layer 20 may be defined as a continuous layer that extends from first end 21 to second end 23 of stent 10 and fully extends across and fills cells or interstices defined between filaments 14 of tubular scaffold 22. However, in other instances coating layer 20 may extend less than the entire length of stent 10, if desired, leaving a portion of cells or interstices defined between filaments 14 of tubular scaffold 22 unfilled or open.

Additionally, FIG. 2 shows a valve 16 positioned within the lumen of stent 10. As will be discussed in greater detail below, valve 16 may be formed as a portion of coating layer 20. In other words, valve 16 may be a unitary or monolithic structure formed in conjunction with forming coating layer 20 on tubular scaffold 22. For example, FIG. 2 illustrates that valve 16 may be an inwardly extending portion of coating layer 20 extending radially inward of tubular scaffold 22 at narrowed or necked region 11. In other words, valve 16 may be defined as a unitary or monolithic portion of coating layer 20 that extends radially inward from an inner surface of tubular scaffold 22 toward the central longitudinal axis 25 of stent 10.

Further, in some examples, valve 16 may be defined as a monolithic portion of coating layer 20 that extends circumferentially within the lumen of stent member 10. In other words, it can be appreciated that valve 16 may be defined as an annular member that extends continuously around the lumen of stent 10 positioned radially inward of tubular scaffold 22 in the narrowed or necked region 11. Further, valve 16 may be defined as an uninterrupted extension of coating layer 20 projecting toward central longitudinal axis 25, forming an annular rim of polymeric material radially inward of tubular scaffold 22 in the narrowed or necked region 11.

As described above, FIG. 2 illustrates that stent 10 may include a first tapered (e.g., conical) region 17 and a second tapered (e.g., conical) region 19 with the narrowed or necked region 11 positioned therebetween. Both first conical region 17 and second conical region 19 may generally be shaped to taper radially inwardly in opposite directions toward the longitudinal axis 25 providing the stent 10 with an hourglass shape. For example, first conical region 17 may taper radially inward from a first transition point 13 along stent 10 to valve 16 while second conical region 19 may taper radially outward from valve 16 to a second transition point 15 along stent 10. For example, the first conical region 17 (including the stent filaments 14 and coating layer 20) may bear some resemblance to a cone-shaped funnel tapering from a wide portion nearest a patient's mouth to valve 16. Further, second conical region 19 (including the stent filaments 14 and coating layer 20) may bear some resemblance to a cone-shaped funnel tapering from valve 16 to a wide portion closer to a patient's stomach. Further, as illustrated in FIG. 2, in a closed configuration, valve 16 may taper inwardly toward central longitudinal axis 25 and close (e.g., contact, seal, etc.) onto itself such that it stops flow of material (e.g., stomach acid) from flowing through the lumen of stent 10. As discussed above, it may be desirable for valve 16 to prevent stomach acids from flowing from a patient's stomach toward the patient's mouth. FIG. 2 shows valve 16 in a closed configuration. The stent 10 may be configured to bias valve 16 to the closed configuration in a nominally deployed state.

As described above, in some instances it may be desirable for valve 16 to expand radially outward to permit nutritional material (e.g., food, water, etc.) to pass through the lumen of stent 10. For example, in some examples it is desirable for valve 16 to radially expand to permit a bolus of food or liquid to pass from a patient's mouth, through the valve 16, to the stomach. As will be described in greater detail below, at least some stent and valve examples disclosed herein may include stent filaments of tubular scaffold 22 which impart a radially compressive force inward on valve 16 to maintain the valve 16 in a closed configured while in a "nominally-deployed" state (e.g., a state in which no outside forces are acting on the stent 10 to move the valve 16 to an open configuration).

Further, the compressive force exerted by filaments 14 of tubular scaffold 22 on valve 16 must be low enough such that normal, peristaltic contractions associated with normal digestive processing (e.g., normal eating and digesting of food) will open valve 16, thereby permitting the bolus of nutritional material to pass through valve 16 and into the stomach (while also permit vomiting contractions to expel food back through valve 16). However, this compressive force must also be large enough to ensure the valve 16 reverts to the closed configuration when in the nominally deployed state such that stomach acids will not leak through the valve 16 from the stomach, causing symptoms of acid reflux.

Therefore, in at least some examples a threshold radially inward compressive force may be imparted by the filaments 14 onto the valve 16 in the nominally deployed state to hold the valve 16 in the closed configuration. In other words, stent 10 (including the radial compression of filaments 14) must be designed such that valve 16 remains closed in a nominally deployed state, yet opens when peristatic forces greater than the threshold inward compressive force are imparted onto the valve 16 (e.g., when peristaltic forces push a bolus of food or liquid through the valve aperture 124, thereby causing radially outward expansion forces of greater than the threshold inward compressive force to be imparted to the scaffold 22) to overcome the radially inwardly compressive forces biasing the valve 16 to the closed configuration. In some instances, the threshold inward compressive force may be less than $0.900$ $N/cm^2$, less than $0.800$ $N/cm^2$, less than $0.700$ $N/cm^2$, less than $0.600$ $N/cm^2$, less than $0.500$ $N/cm^2$, or less than $0.400$ $N/cm^2$. Furthermore, forces less than the threshold inward compressive force (such as those imparted onto the valve 16 via acid reflux) will not cause valve 16 to open, thereby preventing stomach acids from flowing from the stomach into the esophagus. In some instances, the threshold inward compressive force may be at least $0.200$ $N/cm^2$, at least $0.300$ $N/cm^2$, at least $0.400$ $N/cm^2$, at least $0.500$ $N/cm^2$, at least $0.600$ $N/cm^2$, at least $0.700$ $N/cm^2$, or at least $0.800$ $N/cm^2$. In some instances, the threshold inward compressive force may be in the range of between $0.200$ $N/cm^2$ to $0.900$ $N/cm^2$, in the range of between $0.200$ $N/cm^2$ to $0.800$ $N/cm^2$, in the range of between $0.300$ $N/cm^2$ to $0.900$ $N/cm^2$, in the range of between $0.300$ $N/cm^2$ to $0.800$ $N/cm^2$, in the range of between $0.400$ $N/cm^2$ to $0.800$ $N/cm^2$, in the range of $0.400$ $N/cm^2$ to $0.700$ $N/cm^2$, for example.

Figure 3:
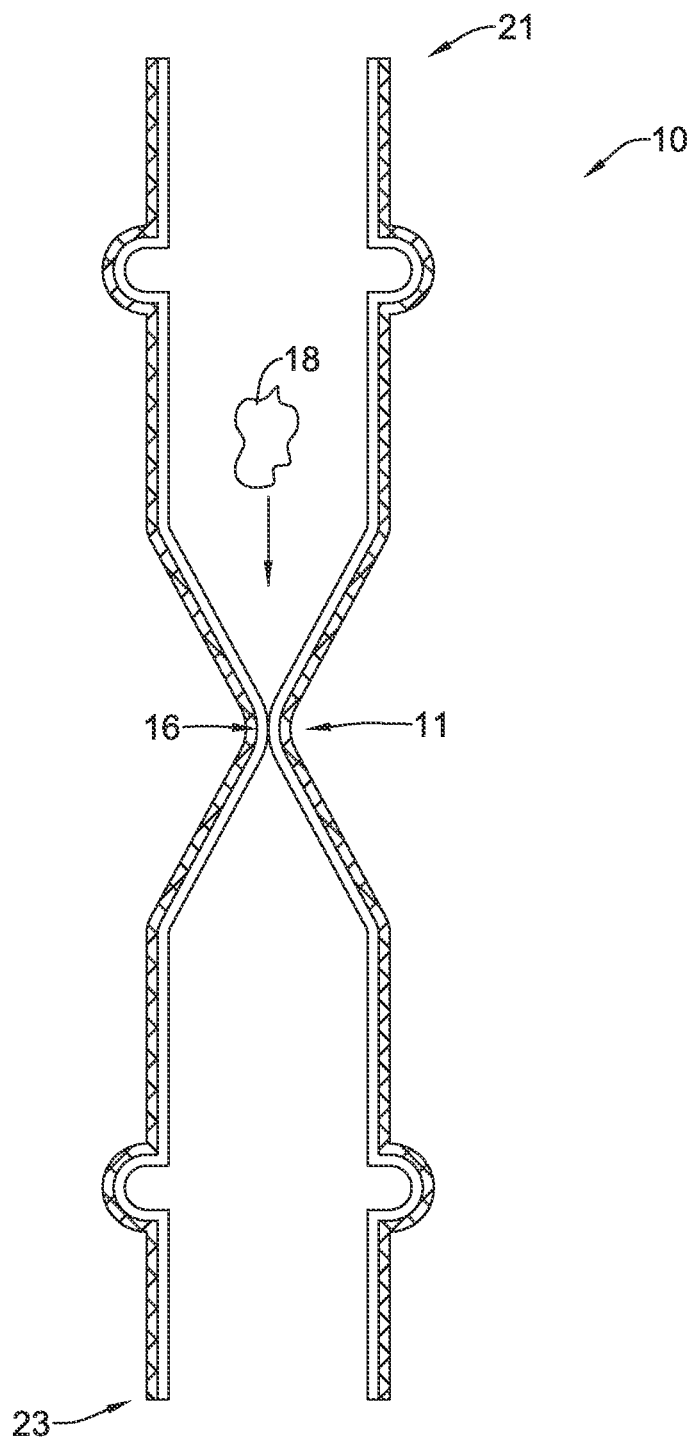
FIGS. 3 and 4 are cross-sectional views of the stent of FIG. 1 illustrating material passing through the valve.
Figure 4:
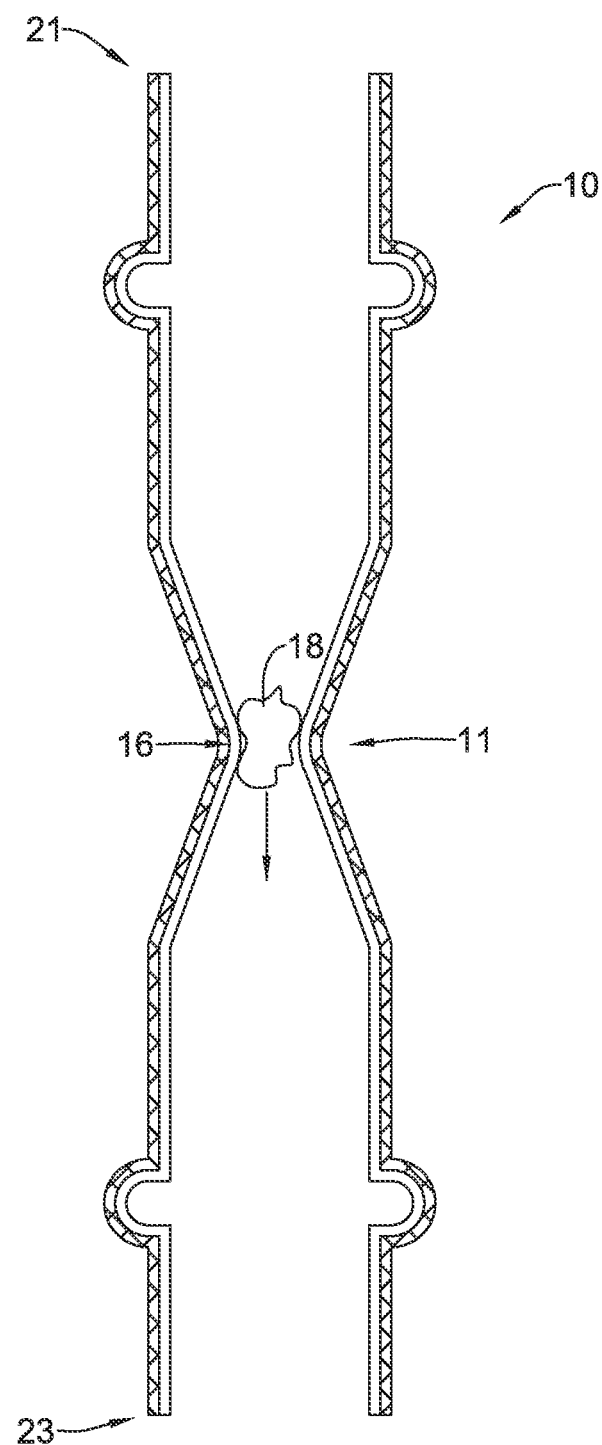

FIG. 3 and FIG. 4 illustrate valve 16 expanding radially outward to allow a bolus of nutritional material (e.g., food) 18 to pass through the lumen of stent 10 and through valve 16. As shown by the arrow in FIG. 3, and, in general, bolus of nutritional material 18 may flow through stent 10 from a first end 21 (e.g., the end closest to a patient's mouth) to a second end 23 (e.g., the end closest to a patient's stomach). FIG. 4 illustrates that valve 16 may permit the material 18 to pass through the lumen of the stent 10 by expanding radially outward as the material 18 passes through valve 16. While not shown in FIG. 4, it is contemplated that in some examples valve 16 may conform to the shape of material 18 as it passes through valve 16.

Figure 5:
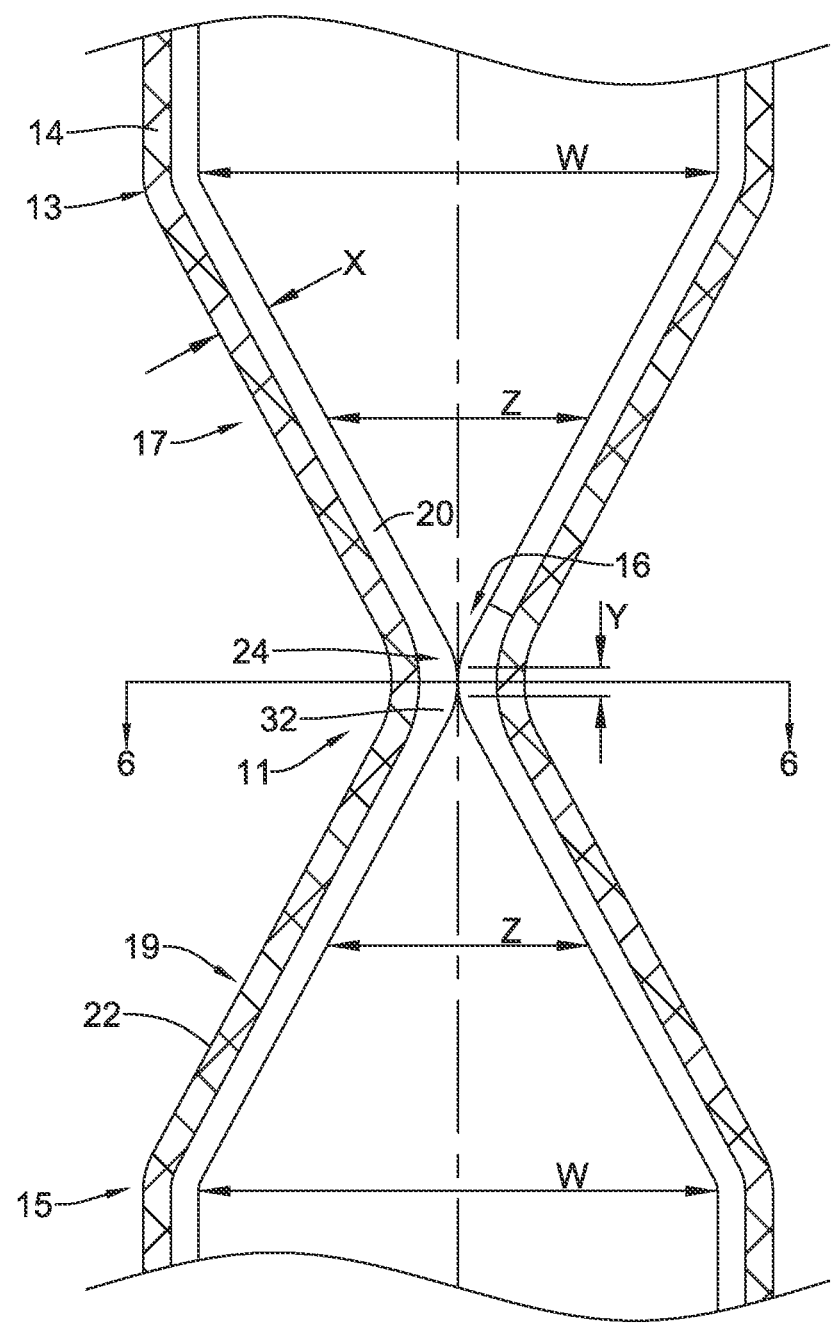
FIG. 5 is an enlarged cross-sectional view of a portion of the stent of FIG. 1 including the valve in a closed configuration.

FIG. 5 illustrates an enlarged and detailed view of example stent 10 including tubular scaffold 22 and valve 16. As described above, stent 10 may include a coating layer 20 covering tubular scaffold 22 and forming valve 16. For example, FIG. 5 illustrates that coating layer 20 may include a thickness depicted as "X" extending along a substantial portion and covering filaments 14, such as covering an inner surface and/or outer surface of filaments 14. For illustrative purposes, coating layer 20 is shown extending along inner surface of tubular scaffold 22, however, it is noted that additionally or alternatively coating layer 20 may extend along outer surface of tubular scaffold in some embodiments. In some examples, the coating layer 20 may be formed from a silicone material or a polyurethane material, for instance.

Further, as shown in FIG. 5 (and illustrated further in FIG. 6), the coating layer 20 may extend radially inward from the inner surface of tubular scaffold 22 to form the valve 16 at narrowed or necked region 11 of stent 10. As will be further illustrated in FIG. 6, valve 16 may have an annular shape and include a circumferential, curvilinear surface extending around the longitudinal axis 25 of stent 10 whereby the coating layer 20 extends away from the inner surface of the wall of the tubular scaffold 22 (e.g., radially inward toward the longitudinal axis 25) to form valve 16. As illustrated in FIG. 5, valve 16 may include a thickness depicted as "Y" in FIG. 5.

FIG. 5 illustrates that in some instances the thickness "Y" of valve 16 may be substantially equal to the thickness "X" of coating layer 20. In other words, coating layer 20 may maintain a substantially uniform thickness "X" along the length of scaffold 22 which extends uniformly to form the thickness "Y" of valve 16. However, in other embodiments the wall thickness "X" of coating layer 20 and/or the thickness "Y" defining valve 16 may be different. For example, some portions of coating layer 20 and/or the thickness defining valve 16 may be thinner or thicker than other portions along stent 10.

Similar to that shown in FIG. 2, FIG. 5 illustrates the first tapered region 17 and the second tapered region 19, both of which may bear some resemblance to a cone-shaped funnel and together form an hourglass shape. For example, stent 10 (including tubular scaffold 22 and coating layer 20) may taper radially inward from a first transition point 13 toward valve 16. Valve 16 includes a valve aperture 24. Valve aperture 24 may be defined as the "opening" of valve 16 (e.g., the opening of valve 16 through which nutritional material may flow). As illustrated in FIG. 5, valve aperture 24 may be aligned with the central longitudinal axis 25.

FIG. 5 further illustrates stent 10 (including scaffold 22 and coating layer 20) tapering radially inward from a second transition point 15 toward valve 16. Further, both the first tapered region 17 and the second tapered region 19 may include a wide portion having an inner diameter (depicted in FIG. 5 as dimension "W") tapering to a narrower portion having an inner diameter (depicted in FIG. 5 as dimension "Z") less than the inner diameter of the wide portion. As shown in FIG. 5, the wide portion of each of the first tapered region 17 and the second tapered region 19 may be positioned adjacent to first transition point 13 and second transition point 15, respectively. Further, the narrower portion may be positioned closer to valve 16.

Figure 6:
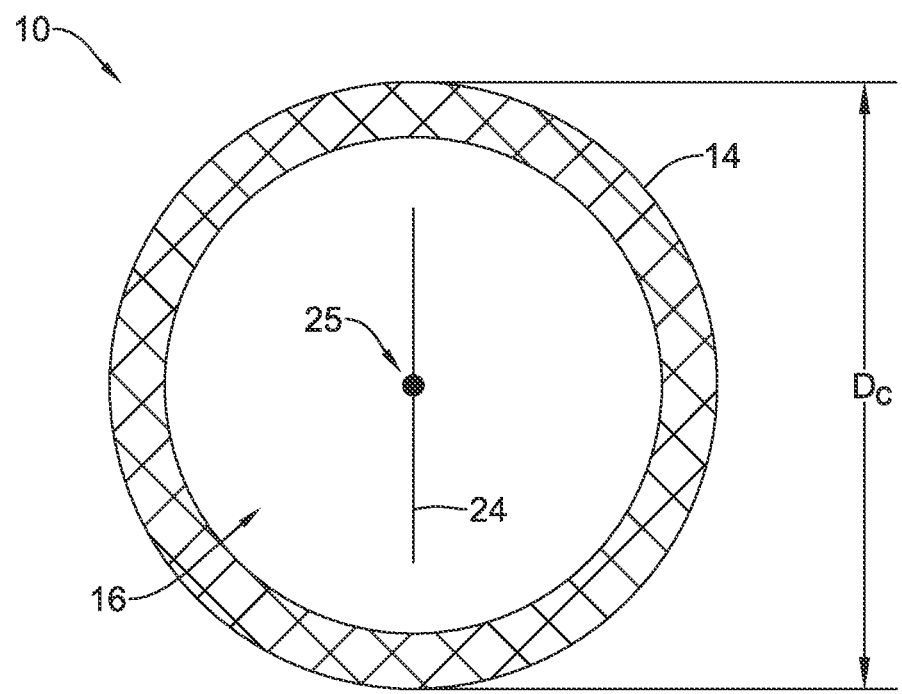
FIG. 6 is a cross-sectional view of the stent and valve of FIG. 5 taken along line 6-6 of FIG. 5.

FIG. 6 shows a cross-sectional view of stent 10 through narrowed region 11 and valve 16 taken along line 6-6 of FIG. 5. In particular, line 6-6 of FIG. 5 intersects valve aperture 24 of valve 16 described above. As shown in FIG. 6, valve aperture 24 may intersect the longitudinal axis 25 of stent 10. As described above, FIG. 6 depicts valve 16 in a closed configuration whereby filaments 14 (defining scaffold 22 described above) are imparting a radial inward compressive force onto valve 16, thereby maintaining valve aperture 24 in a closed configuration. FIG. 6 illustrates that narrowed region 11 of stent 10 may include an outer diameter which is depicted as "$D_C$" in FIG. 6 in the closed configuration. The closed configuration of valve 16 may be defined as a configuration which the valve aperture 24 is closed and prevents material from flowing through the valve aperture 24. As described above, FIG. 6 shows the shape of valve 16 as substantially circular and extending circumferentially around the longitudinal axis 25 of the stent 10.

Figure 7:
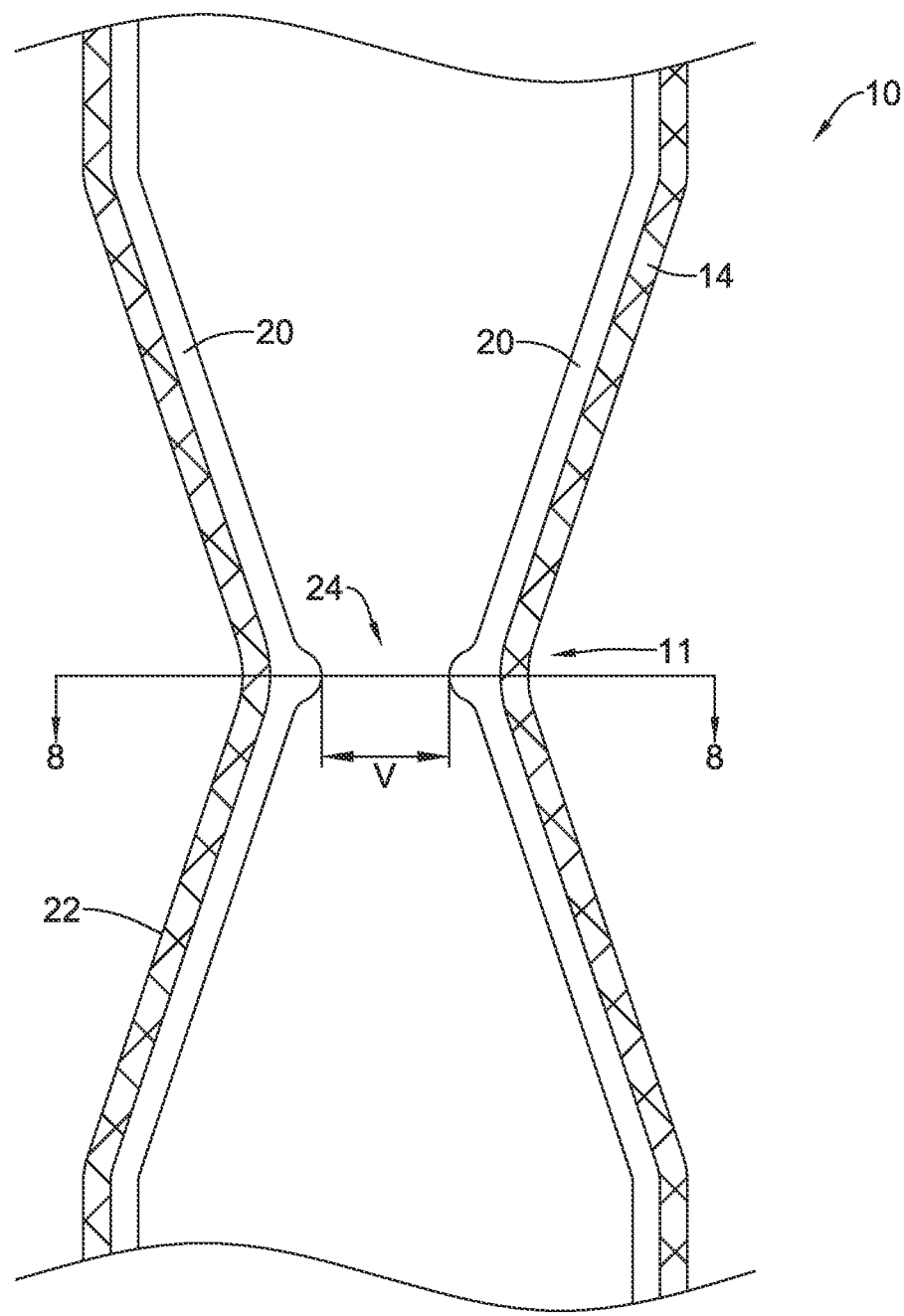
FIG. 7 is an enlarged cross-sectional view of a portion of the stent of FIG. 1 including the valve in an open configuration.

FIG. 7 shows an enlarged view of stent 10 described above with valve 16 in an open configuration. For example, FIG. 7 shows valve aperture 24 opened to a width depicted as dimension "V" in FIG. 7. As discussed above, it can be appreciated that valve aperture 24 may open via a force being imparted radially outward (e.g., a force generated via nutritional material being driven through the valve 16 via peristalsis) which is large enough to overcome the radially inward compressive force (described above) imparted by filaments 14 of tubular scaffold 22 described above.

Figure 8:
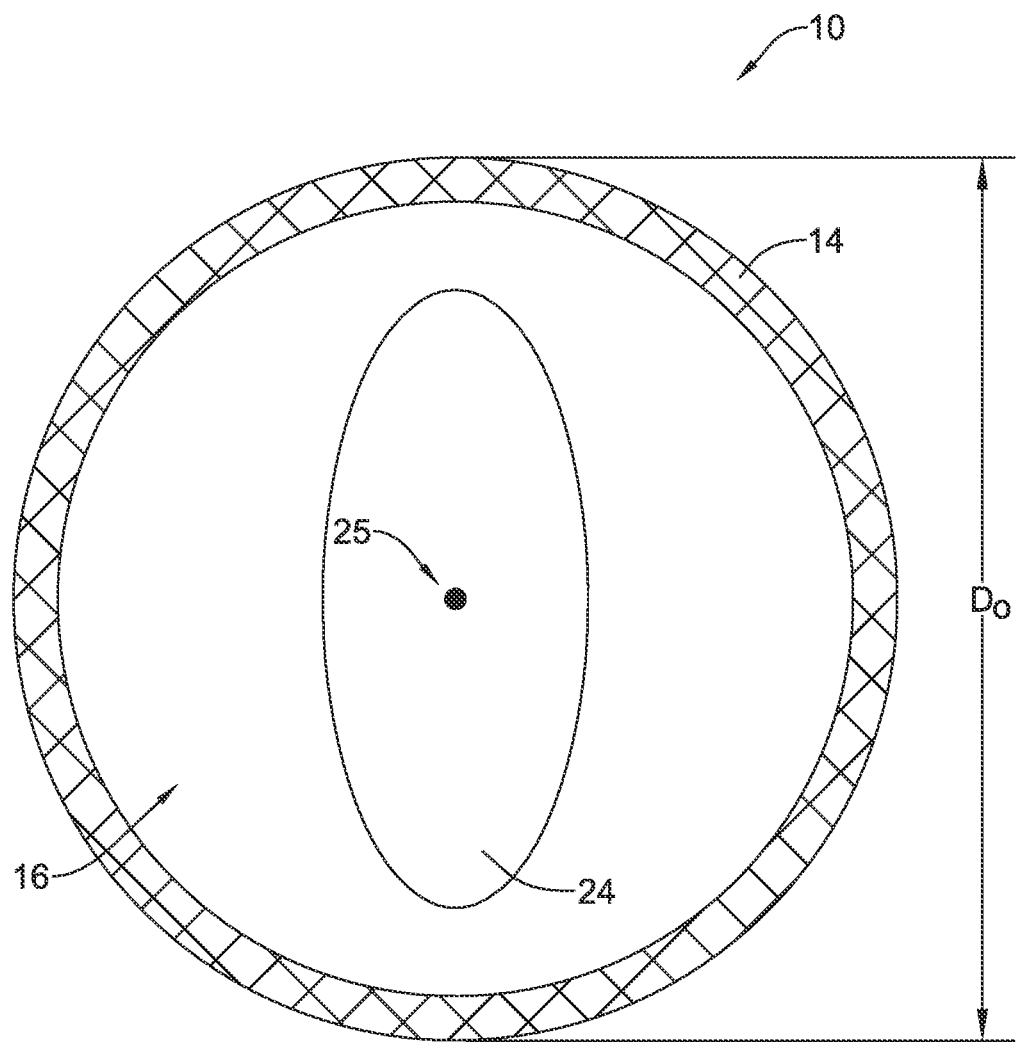
FIG. 8 is a cross-sectional view of the stent and valve of FIG. 7 taken along line 8-8 of FIG. 7.

FIG. 8 shows a cross-sectional view of the stent 10 through narrowed region 11 and valve 16 taken along line 8-8 of FIG. 7. FIG. 8 further illustrates the valve 16 in an open configuration. In other words, FIG. 8 shows narrowed region 11 of stent 10 being expanded to an outer diameter depicted as "$D_O$" in FIG. 8. Diameter $D_O$ may be greater than diameter $D_C$ described above with respect to FIG. 6. It can be appreciated that as narrowed region 11 of stent 10 expands due to peristaltic forces acting thereupon, the outer diameter of narrowed region of stent 10 may increase from diameter $D_C$ depicted in FIG. 6 to diameter $D_O$ depicted in FIG. 8. Accordingly, as the outer diameter of narrowed region of stent 10 increases from diameter $D_C$ depicted in FIG. 6 to diameter $D_O$ depicted in FIG. 8, valve 16 (including valve aperture 24) may shift from a closed configuration to an open configuration. Likewise, tubular scaffold 22 radially expands in narrowed region 11 between the closed configuration to the opened configuration.

Additionally, line 8-8 of FIG. 7 transects the valve aperture 24 described above. FIG. 8 illustrates the valve 16 extending radially inward from stent filaments 14 (defining scaffold 22 described above). As shown in FIG. 8, valve aperture 24 may be an opening centered about the central longitudinal axis 25 of the lumen of stent 10. However, while the figures described herein depict example valves and related elements centered about the central longitudinal axis 25, it is contemplated that any of the examples described herein may be designed such that the structural elements defining any portion of stent 10 and/or valve 16 may be off-center. In other words, valve 16 may be asymmetrical about the central longitudinal axis 25 in one or more examples described herein.

Additionally, FIG. 8 shows that valve aperture 24 may be substantially ovular (e.g., elliptically) shaped in the open configuration. The ovular shape of the valve aperture 24 may reduce the force required to maintain valve 16 in closed configuration while also permitting valve 16 to open via peristaltic forces acting upon valve 16 as described above. While the example shown in FIG. 8 illustrates an ovular-shaped valve aperture 24, other examples are contemplated in which the shape of valve aperture 24 may be circular, triangular, star-shaped, square, rectangular, etc. Additionally, in some examples the valve aperture 24 may include one or more structures including flaps, leaflets, channels, slits, cuts, grooves, etc. Further, valve aperture 24 designs which combine the various geometric shapes, orientations and structures are contemplated.

Figure 9:
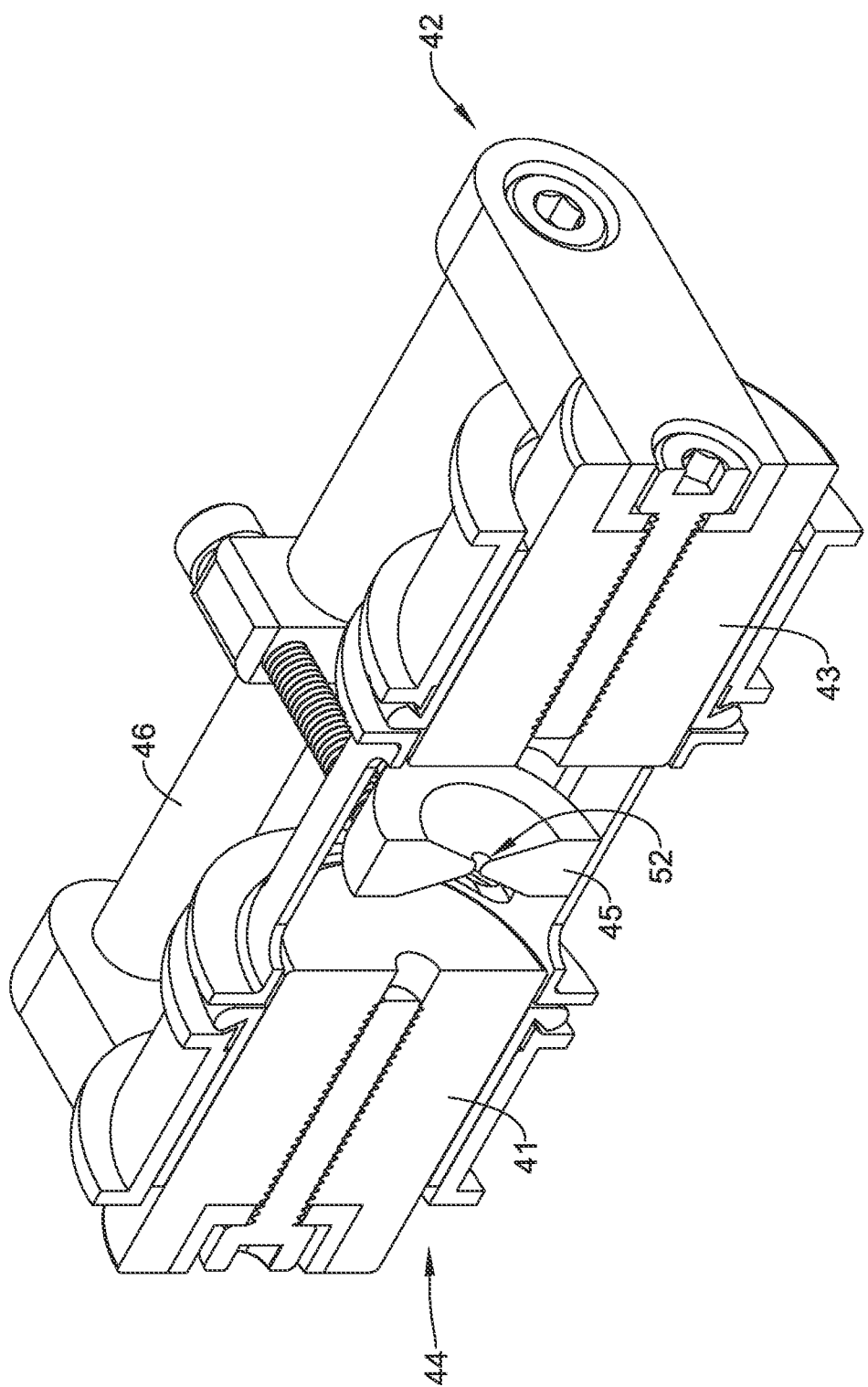
FIG. 9 is a cross-sectional perspective view of an example shaping mandrel and fixture device.
Figure 10:
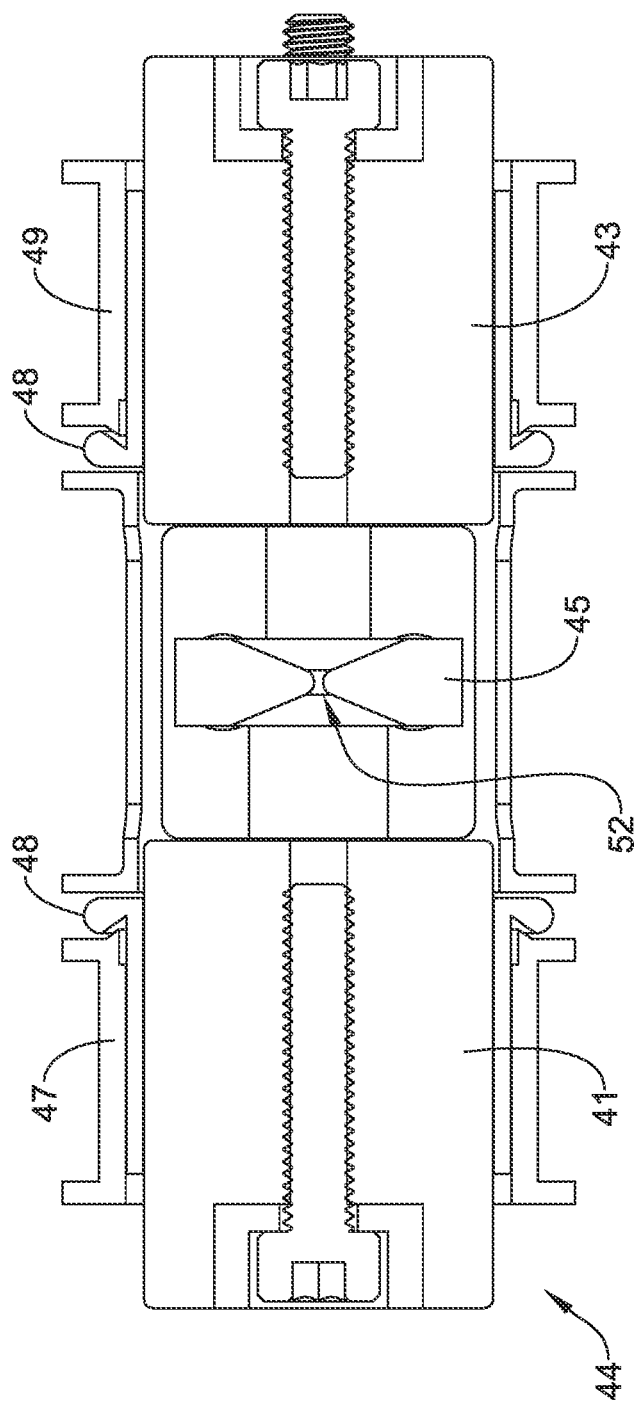
FIG. 10 is another cross-sectional view of the shaping mandrel and fixture device shown in FIG. 9.
Figure 11:
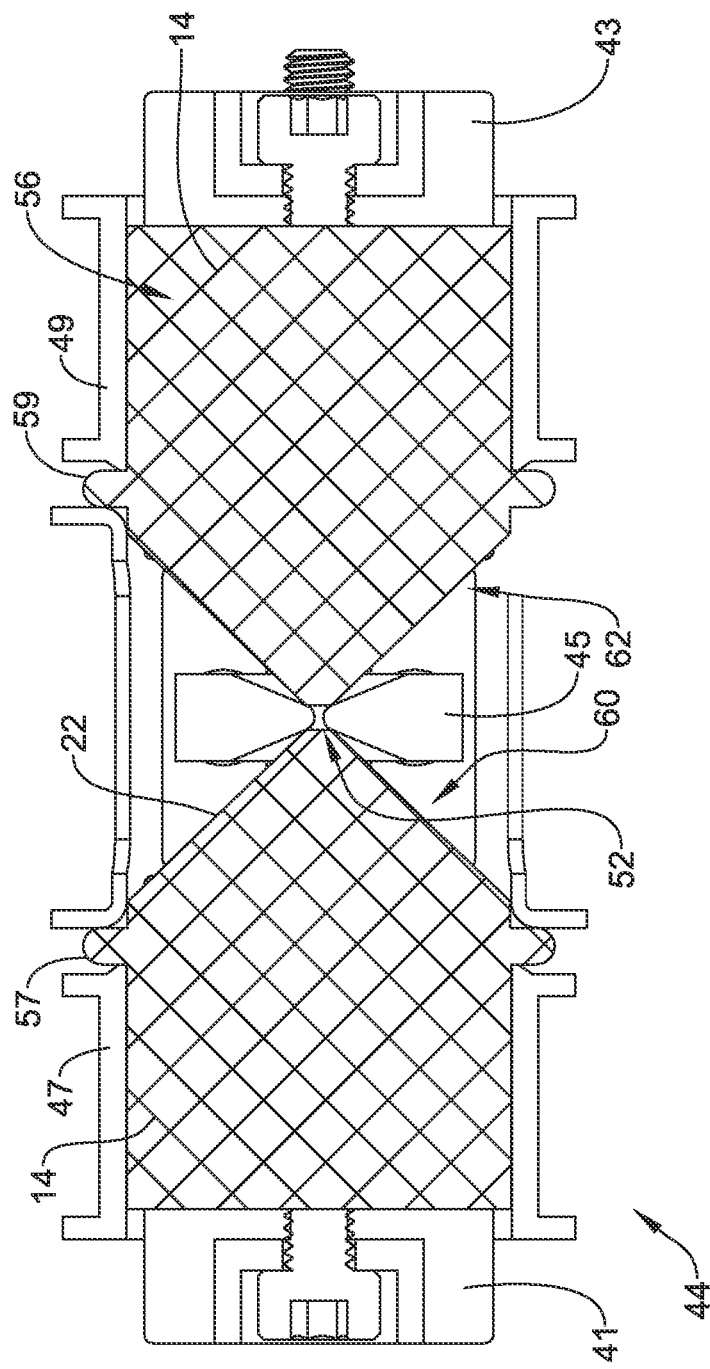
FIG. 11 is a cross-sectional view of the shaping mandrel and fixture device shown in FIG. 9 with a stent positioned thereon.

FIGS. 9-11 illustrates an example device and method for forming (e.g., heat setting) the stent structure including stent scaffold 22 formed from filaments 14 as shown and described above. For example, FIG. 9 illustrates an example stent shaping mandrel 44 which is mounted on (e.g., engaged with) an external stent fixture device 42. As illustrated in FIG. 9, stent shaping mandrel 44 may include a first mandrel segment 41 and a second mandrel segment 43. External stent fixture 42 may hold first mandrel segment 41 in a fixed position relative to second mandrel segment 43 with a gap between first mandrel segment 41 and second mandrel segment 43 such that first mandrel segment 41 is spaced away from second mandrel segment 43 and not directly contacting one another. Additionally, shaping mandrel 44 may further include a compressive member 45. Compressive member 45 may be positioned in the gap between the first mandrel segment 41 and the second mandrel segment 43. Compressive member 45 may include a narrowed aperture (e.g., opening, pinch point, etc.) 52. In some instances, compressive member 45 may comprise a plurality of circumferentially arranged dies circumferentially arranged about a central longitudinal axis extending through first and second mandrel segments 41, 43. The plurality of dies may be radially movable toward and away from central longitudinal axis to adjust the size of the narrowed aperture 52.

As will be illustrated and described below, stent shaping mandrel 44 may be utilized to change the shape (e.g., form) of a straight, cylindrical tubular, braided stent scaffold into a more complex-shaped stent scaffold such as stent scaffold 22 shown in FIG. 1 (which includes enlarged portions 12, tapered portions 17/19 and narrowed region 11). In order to form the complex scaffold 22 shape illustrated in FIG. 1, it may be desirable to utilize a stent fixture device 42 to manipulate the various components of the shaping mandrel 44 shown in FIG. 9. For example, the fixture device 42 may include a frame 46 attached between first mandrel segment 41 and second mandrel segment 43 and maintain first and second mandrel segments 41, 43 a fixed distance apart. In some instances, frame 46 may include an adjustment mechanism (e.g., an adjustment screw) which may allow a user to adjust the distance between the first mandrel segment 41 and the second mandrel segment 43 to a desired fixed distance. Additionally, adjusting the distance between the first mandrel segment 41 and the second mandrel segment 43 may also alter their distance from the compressive member 45. The distance between the first mandrel segment 41 and the second mandrel segment 43 may control the shape of the first tapered region 17 and the second tapered region 19 described above with respect to FIG. 2.

FIG. 10 illustrates a cross-sectional view of the shaping mandrel 44 shown in FIG. 9. FIG. 10 shows shaping mandrel 44 removed from the fixture device 42 described above. As described above, FIG. 10 shows shaping mandrel 44 including first mandrel segment 41, second mandrel segment 43 and compressive member 45 (positioned between first mandrel segment 41 and second mandrel segment 43). As described above, FIG. 10 shows that the compressive member 45 may include a narrowed aperture 52 (e.g., opening, pinch point, etc.). It can be appreciated that the narrowed aperture 52 of compressive member 45 may be utilized to form the narrowed region 11 of the tubular scaffold 22 shown in FIG. 1. The narrowed region 11 of tubular scaffold 22 of FIG. 1 may be referred to as a "necked" region. Additionally, FIG. 10 illustrates that shaping mandrel 44 may include a first raised annular rim 48 and a second raised annular rim 48. First annular rim 48 may be provided with first mandrel segment 41 and second annular rim 48 may be provided with second mandrel segment 43. As will be shown and described below with respect to FIG. 11, first and second raised annular rims 48 may be utilized to form the enlarged portions 12 or flanges of the tubular scaffold 22 shown in FIG. 1. Furthermore, fixture device may include a first saddle 47 and a second saddle 49 configured to be placed around the first mandrel segment 41 and the second mandrel segment 43, respectively, to clamp a braided tubular scaffold to the shaping mandrel 44. For instance, a first end region of the braided tubular scaffold can be clamped between the first saddle 47 and the first mandrel segment 41 and a second end region of the braided tubular scaffold can be clamped between the second saddle 49 and the second mandrel segment 43.

An example method to form tubular scaffold 22 may include positioning a straight, cylindrical tubular braided scaffold around shaping mandrel 44 (shown in FIG. 11) followed by the application of a heat treatment to anneal the stent filaments 14 (shown in FIG. 11) in a preferred shape (e.g., the shape dictated by the shaping mandrel 44). For example, FIG. 11 illustrates an example cylindrical tubular braided scaffold 56 which has been positioned (e.g., disposed) around first mandrel segment 41 and second mandrel segment 43, having first and second end regions clamped to the first and second mandrel segments 41, 43 with first and second saddles 47 and 49, respectively. Braided tubular scaffold 56 may be formed from one or more interwoven filaments 14 formed into a cylindrical structure. FIG. 11 further illustrates braided scaffold 56 disposed along first mandrel segment 41 and second mandrel segment 43, with raised annular rims 48 positioned in the lumen of the braided scaffold 56 such that filaments 14 of braided scaffold 56 conform to the curvature/shape of the raised annular rims 48. It can be appreciated that first saddle or clamp 47 and second saddle or clamp 49 may be designed to grasp and hold the braided scaffold 56 along the outer surface of both first mandrel segment 41 and second mandrel segment 43, respectively. Additionally, first saddle or clamp 47 may be positioned proximate the first raised annular rim 48 to instill a first ridge portion 57 in the braided scaffold 56 and second saddle or clamp 49 may be positioned proximate the second raised annular rim 48 to instill a second ridge portion 59 in the braided scaffold 56. Both first ridge portion 57 and second ridge portion 59 may extend radially away from other portions of braided scaffold 56. Additionally, both first ridge portion 57 and second ridge portion 59 may extend circumferentially around the outer surface of braided segment 56.

It can be appreciated from FIG. 11 that the shape of each of first ridge portion 57 and second ridge portion 59 may define a particular shape of the tubular scaffold 22 after a heat treatment is applied to the braided cylindrical scaffold 56. For example, after heat treating the braided scaffold 56 shown in FIG. 11, the first ridge portion 57 and second ridge portion 59 may correspond to the enlarged portions or flanges 12 of the tubular scaffold 22 shown in FIGS. 1 and 2. Similarly, it can be appreciated that the outer diameter of first end portion 21 and second end portion 23 of the tubular scaffold 22 shown in FIGS. 1 and 2 may correspond to the outer diameter of first mandrel segment 41 and second mandrel segment 43 shown in FIG. 11.

FIG. 11 further illustrates that shaping mandrel 44 may form a narrowed (e.g., necked) region in braided scaffold 56 by passing stent filaments 14 through the narrowed aperture 52 of the compressive member 45. For example, FIG. 11 illustrates filaments 14 tapering radially inward from first mandrel segment 41 to the narrowed aperture 52 and tapering radially inward from second mandrel segment 43 to the narrowed aperture 52, with filaments of braided scaffold 56 extending through narrowed aperture 52. In some instances, one or more dies of compressive member 45 may be actuated radially inward to radially constrain filaments 14 of braided scaffold 56 at narrowed aperture 52 to a reduced diameter, with tapered portions 60 and 62 on either side of compressive member 45. The compressive member 45 may restrain the diameter of the braided scaffold 56 at the necked region to a diameter of $D_c$ or less of the finished stent 10, as described above. Additionally, it can be appreciated that first tapered portion 60 of braided scaffold 56 and second tapered portion 62 of the braided scaffold 56 may correspond to first tapered region 17 and second tapered region 19 of the tubular scaffold 22 of stent 10 shown in FIG. 1.

With the filaments 14 of the tubular braid scaffold 56 held in a desired configuration with the shaping mandrel 44, the tubular braid scaffold 56 can be subjected to a heat treatment process to anneal the stent filaments 14 in a preferred formed shape. Thereafter, the braided scaffold 56 may be removed from the shaping mandrel 44, while retaining its formed shape to be used as the tubular scaffold 22 of the stent 10.

It can further be appreciated that the configuration that braided scaffold 22 embodies after being removed from the shaping mandrel 44 may be considered its "nominally deployed" configuration. In other words, the heat treatment process applied to the braided scaffold 56 during the forming process described above may impart a shape-memory configuration in which the scaffold 22 will revert to when unconstrained by an external force. This shaped memory configuration may be referred to as the stent's "nominally deployed" configuration. For example, if scaffold 22 is radially expanded to a diameter greater than its "nominally deployed" diameter, it will return to its "nominally deployed" diameter once the force which is maintaining the scaffold in the radially expanded configuration is removed. The nominally deployed configuration is important because it may define the threshold radial force imparted by the stent filaments 14 to maintain valve 16 in a closed configuration. As discussed above, this threshold force is the force for which the peristaltic contractions must overcome in order to open the valve 16. Correspondingly, it provides the force imparted onto the valve 16 to bias the valve in the closed configuration to ensure stomach acids cannot leak back through the valve from the stomach (while a patient is lying down at rest, for example).

Figure 12:
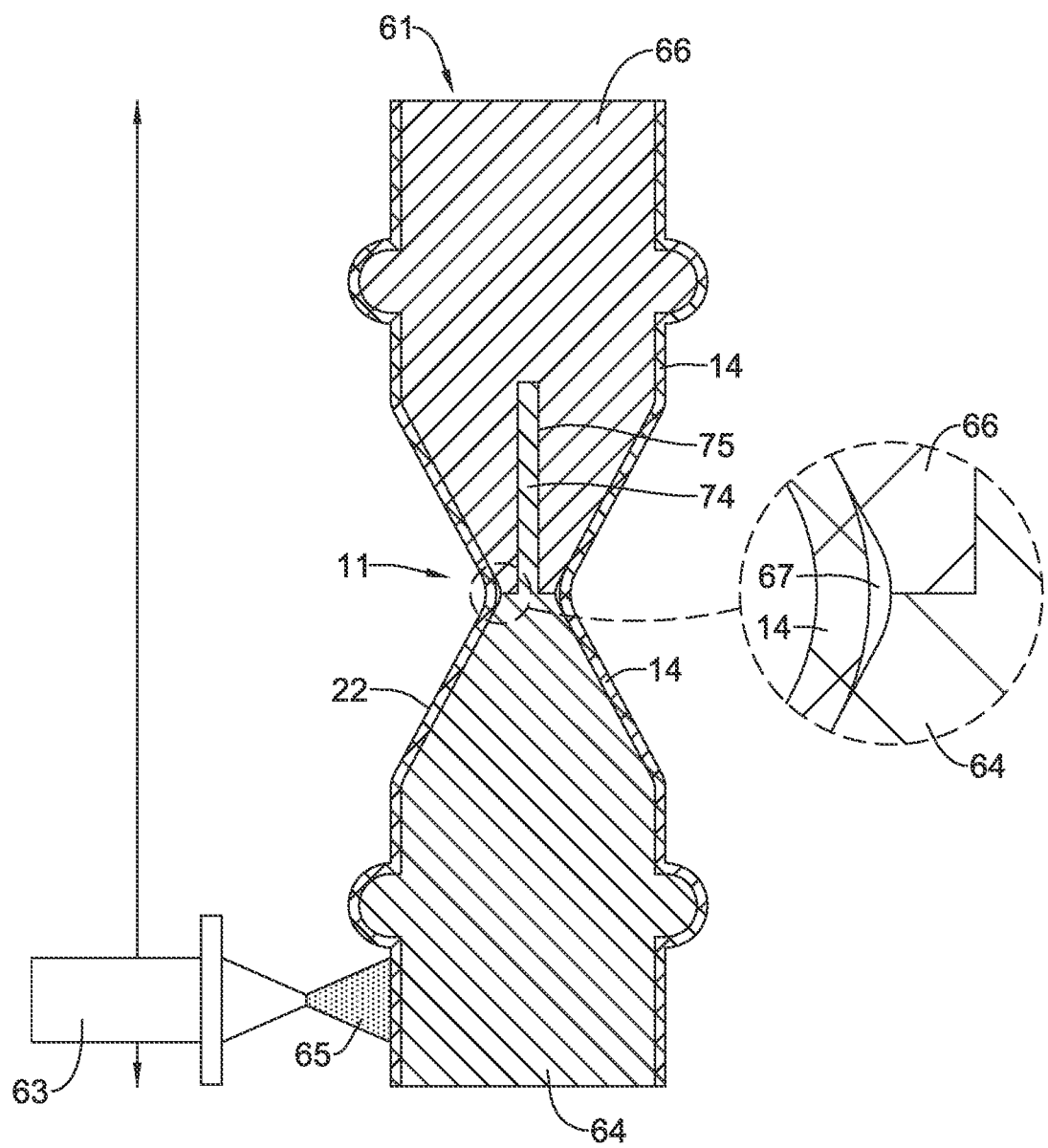
FIGS. 12-13 illustrate an example manufacturing method for forming a valve within an example stent.

FIG. 12 shows method further process for constructing coating layer 20 and valve 16 within braided scaffold 22 (after braided scaffold 56 has been removed from shaping mandrel 44 as described above). As shown in FIG. 12, after being removed from the shaping mandrel 44, braided scaffold 22 may be positioned on a coating mandrel 61. The coating mandrel 61 may be constructed of multiple components to facilitate inserting the coating mandrel 61 into the lumen of the tubular scaffold 22 and through the narrowed region. For example, a first member of the mandrel 61 may be inserted into the lumen of the tubular scaffold 22 from a first end of the tubular scaffold 22 and a second member of the mandrel 61 may be inserted into the lumen of the tubular scaffold 22 from a second end of the tubular scaffold 22. For instance, coating mandrel 61 may include a female member 66 coupled to a male member 64. The male member 64 may include a screw member 74 that may be threaded into a female threaded recess 75 located in female member 66, for example. It can be appreciated that this male-female connection may allow coating mandrel 61 to be easily separated and removed after coating material 65 is applied to braided scaffold 22.

In some instances, the outer diameter of coating mandrel 61 may be larger than the inner diameter of braided scaffold 22 being positioned thereon. It can be appreciated that designing coating mandrel 61 to have a larger outer diameter versus inner diameter of scaffold 22 may result in the scaffold 22 being positioned snug against the outer surface of coating mandrel 61 (FIG. 12 shows scaffold 22 being positioning snug on the outer surface of coating mandrel 61). Further, the larger outer diameter of coating mandrel 61 (as compared to the inner diameter of scaffold 22) may "radially expand" the scaffold 22 as compared to its "nominally deployed" configuration (e.g., nominally deployed diameter) as discussed above. Namely, the coating mandrel 61, extending through the narrowed region 11, radially expands the tubular scaffold 22 at the narrowed region to a diameter greater than its diameter $D_C$ in the nominally deployed configuration in which the valve 16 is in the closed configuration. As will be discussed further with respect to FIG. 13, it can be appreciated that after coating mandrel 61 is removed from the scaffold 22 (after applying the coating layer to the scaffold 22), scaffold 22 may radially compress to its "nominally deployed" configuration (determined via the heat treatment process described above with respect to FIG. 11) to bias the valve 16 to the closed configuration.

Further, it can be appreciated that coating mandrel 61 may be a variety of shapes and/or configurations. For example, coating mandrel 61 may have a profile which substantially matches the profile of the tubular scaffold 22 being positioned thereon. FIG. 12 shows coating mandrel 61 including a profile which substantially matches the profile of the scaffold 22.

FIG. 12 shows spraying element 63 applying a spray coating 65 to scaffold 22 with coating mandrel 61 extending within lumen of scaffold 22. The layer of material applied to scaffold 22 may correspond to coating layer 20 described in the examples above. Further, as shown in FIG. 12, spraying element 63 may translate the full length of scaffold 22 while rotating tubular scaffold 22 and coating mandrel 61 together, depositing material corresponding to coating layer 20 accordingly.

It can further be appreciated that the shape of coating mandrel 61 may define the shape of valve 16. For example, it can be appreciated that spray 65 may pass through the cells of scaffold 22, forming a layer of material on the inner surface of scaffold 22 at locations where scaffold 22 is spaced away from coating mandrel 61. For instance, the detailed view of FIG. 12 shows coating mandrel 61 including a recessed portion 67 spacing the surface of coating mandrel 61 away from tubular scaffold 22 at narrowed region 11. Recessed portion 67 may also be referred to as a "reservoir." Further, recessed portion 67 may extend circumferentially around the entire circumference of coating mandrel 61. Recessed portion 67 may facilitate the formation of a portion of coating layer 20 that extends radially inward from the inner surface of tubular scaffold 22. Accordingly, the shape/contour of coating layer 20 forming the valve 16 may be determined by the profile of recessed portion 67. For example, the cross-sectional shape of recessed portion 67 may be substantially ovular. It can be appreciated that the ovular shape created by recessed portion 67 may correspond to the ovular valve aperture 24 described above. Thus, valve 16 may be formed in the open configuration during the coating process.

FIG. 12 shows that in some instances, the outer surface of coating mandrel 61 will be positioned and/or aligned substantially "flush" with the inner surface of scaffold 22. Depositing coating layer 65 along portions of coating mandrel 61 which are substantially flush with the interior surface of scaffold 56 may cause coating layer 20 to adhere to and/or form an integral interface with the inner surface of tubular scaffold 22 with the coating layer 20 filling open cells or interstices of tubular scaffold 22. As discussed above, applying spray 65 along portions of coating mandrel 61 which are not substantially flush with the interior surface of scaffold 22 (e.g., recessed portion 67) may result in spray 65 passing through the cell openings of scaffold 22 and being deposited along the surfaces coating mandrel 61. It can be appreciated that the recessed portions 67 of coating mandrel 61 may allow space for spray 65 to extend radially inward beyond the inner surface of scaffold 22 such that the coating layer 20 is molded according to the shape of the recessed portion 67. It can be further appreciated from FIG. 12 that coating layer 20 applied along surface of recessed portion 67 may, therefore, form the radially inward extending portions of valve 16 (including ovular aperture 24) described above.

Figure 13:
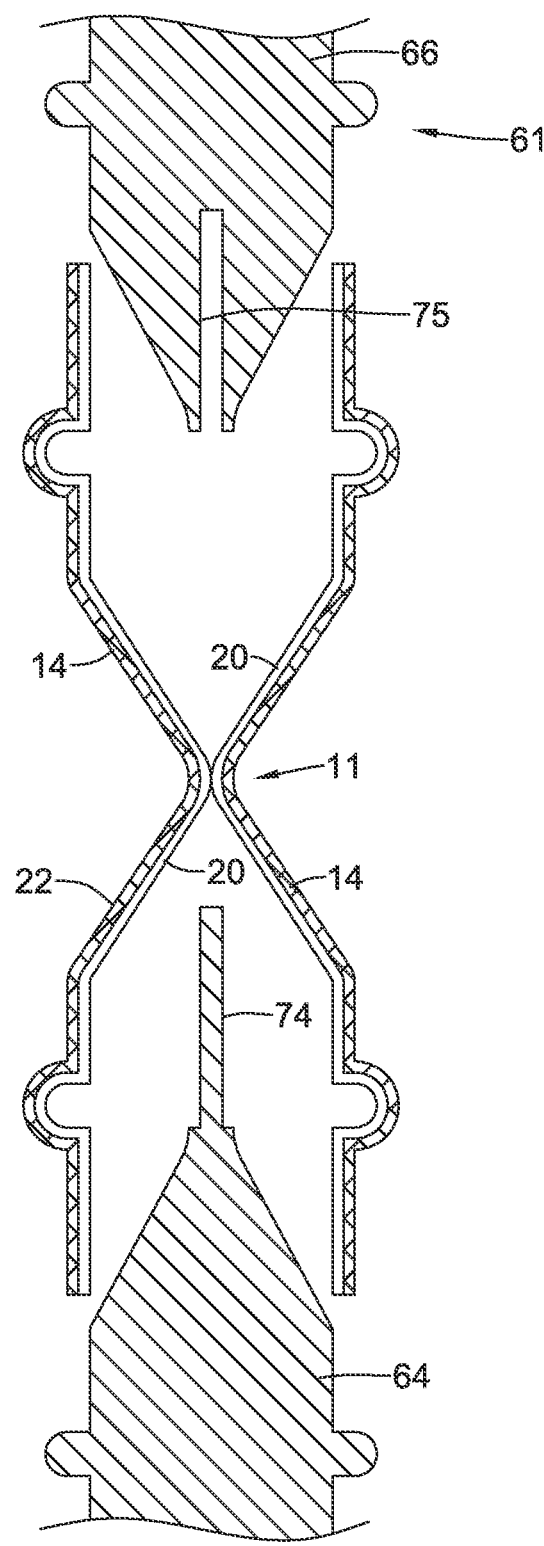

FIG. 13 shows scaffold 22 after coating mandrel 61 (e.g., coating mandrel 61 described with respect to FIG. 12) has been removed. As discussed above, components of mandrel 61 (i.e., first and second members 64, 66) may be separated to remove coating mandrel 61 from lumen of tubular scaffold 22 to provide stent 10 including scaffold 22 and coating layer 20. For instance, male member 64 may be unscrewed from the female member 66 and separated therefrom.

As described above, after stent 10 is removed from coating mandrel 61, tubular scaffold 22 may radially compress and return to its "nominally deployed" configuration. In other words, filaments 14 may radially compress narrowed region 11 inward to return the scaffold 22 to its nominally deployed configuration described above and collapse the valve 16 to its closed configuration. Valve 16 may be formed from a deflectable and/or compressible material which would deform as coating mandrel 61 is removed from scaffold 22. For example, after valve 16 has been constructed according to the method described with respect to FIG. 12, its flexibility may permit the valve aperture 24 (described above but not shown in FIG. 12) to close in response to scaffold 22 radially compressing and returning to its nominally deployed configuration.

Figure 14:
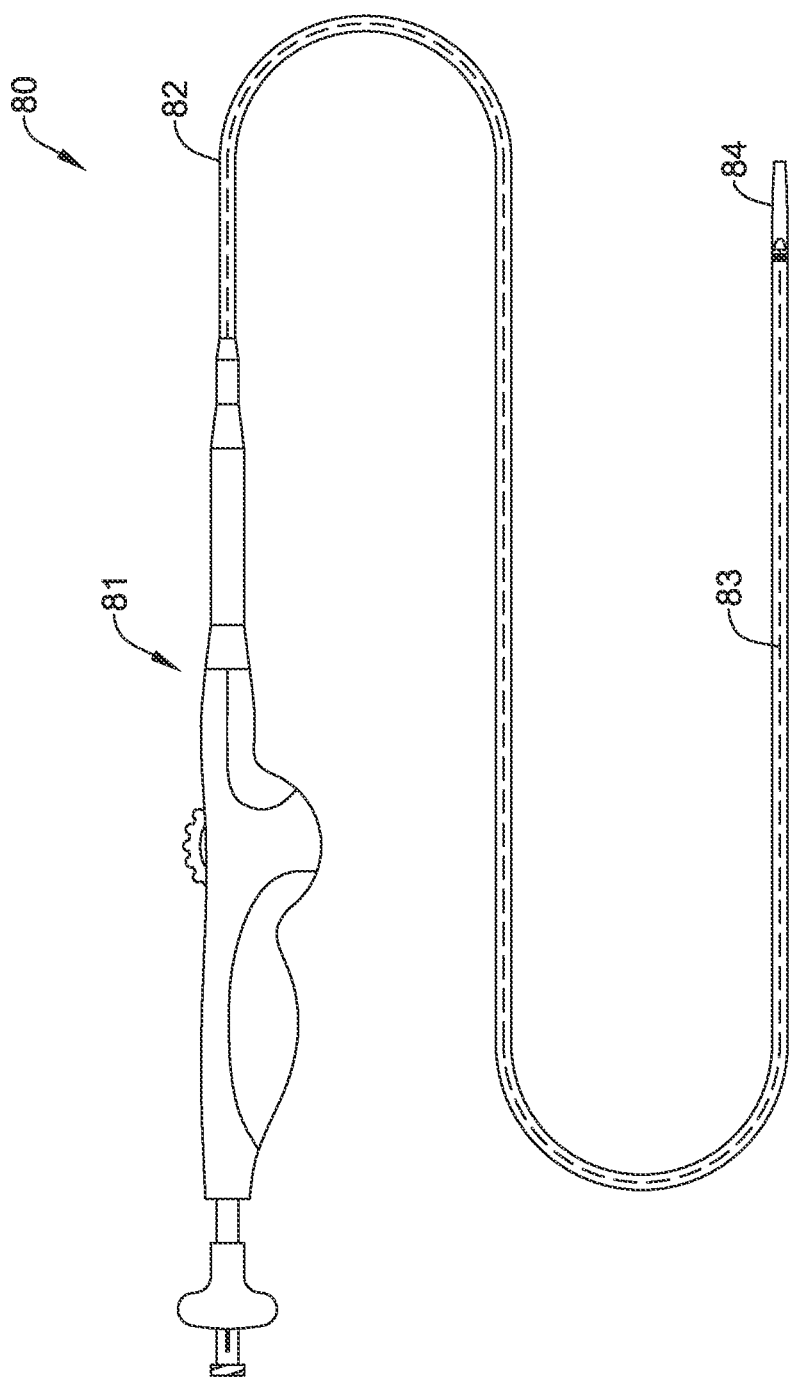
FIG. 14 is an example stent delivery system.

FIG. 14 illustrates an example stent delivery system 80. Stent delivery system may be utilized to advance and position the stent 10 described above. Accordingly, stent delivery system may include a handle member 81 coupled to an outer tubular member 82 and/or an inner member 83. The inner member 83 may extend through the lumen of outer tubular member 82 and is depicted as a dotted line extending through a lumen of outer tubular member 82). The inner member 83 may be coupled to a tip member 84.

Figure 15:
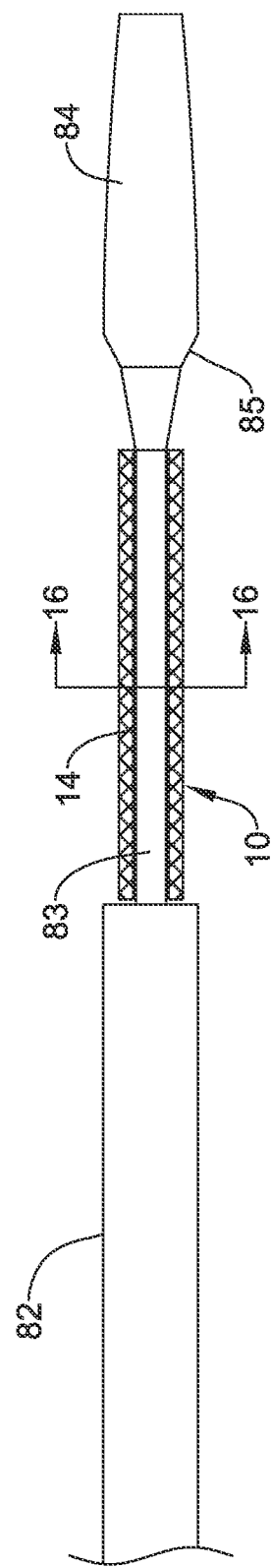
FIG. 15 is a plan view of the stent delivery system shown in FIG. 14 with the outer member retracted.

FIG. 15 illustrates stent 10 positioned over (e.g., surrounding) the inner member 83 (it is noted that the outer tubular member 82 may surround a portion of stent 10 and is shown in a partially retracted configuration for simplicity). As will be described in greater detail below, the inner member 83 may extend through the lumen of stent 10 (including the valve aperture 24 described above). It can further be appreciated that the handle member 81 may be utilized to retract the outer tubular member 82 relative to stent 10, inner member 83 and tip member 84 to deploy the stent 10.

As shown in FIG. 15, the tip member 84 may include one or more tapered portions 85 designed to allow the tip to be easily retracted back through the lumen of stent 10 after stent 10 has been deployed at a target site. This feature is important because valve 16 of stent 10 may be radially compressed on inner member 83 when loaded on the inner member 83 with the inner member 83 extending through valve 16. Therefore, tapered portions 85 are designed to minimize chance that tip member 84 may engage and interfere with the positioning of stent 10 as tip member 84 is retracted through the lumen of stent 10, and through valve 16.

Figure 16:
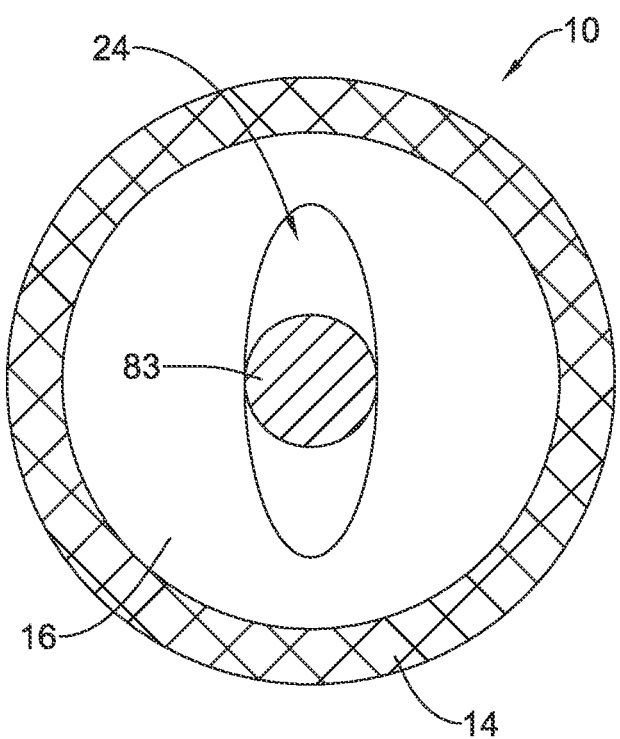
FIG. 16 is a cross-sectional view of the stent and valve of FIG. 15 taken along line 16-16 of FIG. 15.

FIG. 16 is a cross-sectional view taken along line 16-16 of FIG. 15. As described above, FIG. 16 shows stent 10 including filaments 14 encircling valve 16. Valve 16 may extend radially inward from the inner surface of the filaments 14 and includes an ovular valve aperture 24 through which the inner member 83 extends. As described above, valve 16 of stent 10 may be radially compressed on the inner member 83 in its "nominally deployed" configuration. In this configuration, the valve 16 (via the filaments 14) may exert a radially compressive force onto the surface of the inner member 83.

As discussed above with respect to FIG. 1, FIG. 3 and FIG. 4, valve 16 may expand radially outward to allow a bolus of nutritional material (e.g., food) 18 to pass through the lumen of stent 10 and through valve 16. Further, as discussed with respect to FIG. 2, in some instances it may be desirable for the valve 16 to expand radially outward to permit nutritional material (e.g., food, water, etc.) to pass through the lumen of stent 10. For example, the stent filaments of tubular scaffold 22 which impart a radially compressive force inward on valve 16 may maintain the valve 16 in a closed configured while in a "nominally-deployed" state (e.g., a state in which no outside forces are acting on the stent 10 to move the valve 16 to an open configuration). However, the compressive force exerted by filaments 14 of tubular scaffold 22 on valve 16 must be low enough such that normal, peristaltic contractions associated with normal digestive processing (e.g., normal eating and digesting of food) will open valve 16, thereby permitting the bolus of nutritional material to pass through valve 16 and into the stomach (while also permit vomiting contractions to expel food back through valve 16.

To that end, when designing stent 10 (shown in FIG. 1), it may be beneficial to understand the radially outward forces generated by a bolus of nutritional material passing through portions of stent 10. For example, it may be beneficial to understand the minimum radially outward forces generated by a bolus of nutritional material passing through the narrowed region 11 of the stent 10. It can be appreciated from the above discussion that the minimum radially outward forces generated by the bolus of material passing through the narrowed region 11 of the stent 10 may correspond to the maximum compressive forces exerted by filaments 14 of the tubular scaffold 22 on the valve 16. For example, in some instances that stent 10 may be designed such that the maximum compressive forces exerted by filaments 14 of tubular scaffold 22 on valve 16 must be low enough to permit the minimum radially outward force generated by bolus of material to pass through the stent 10. For instance, the stent 10 may be designed such that the maximum radially compressive force exerted by the filaments 14 of tubular scaffold 22 on valve 16 to close the valve 16 in a nominally-deployed state are less than the minimum radially outward force generated by a bolus of material passing through the stent 10, in order to ensure the valve 16 opens sufficiently to allow the bolus of material to pass through the stent 10.

Figure 17:
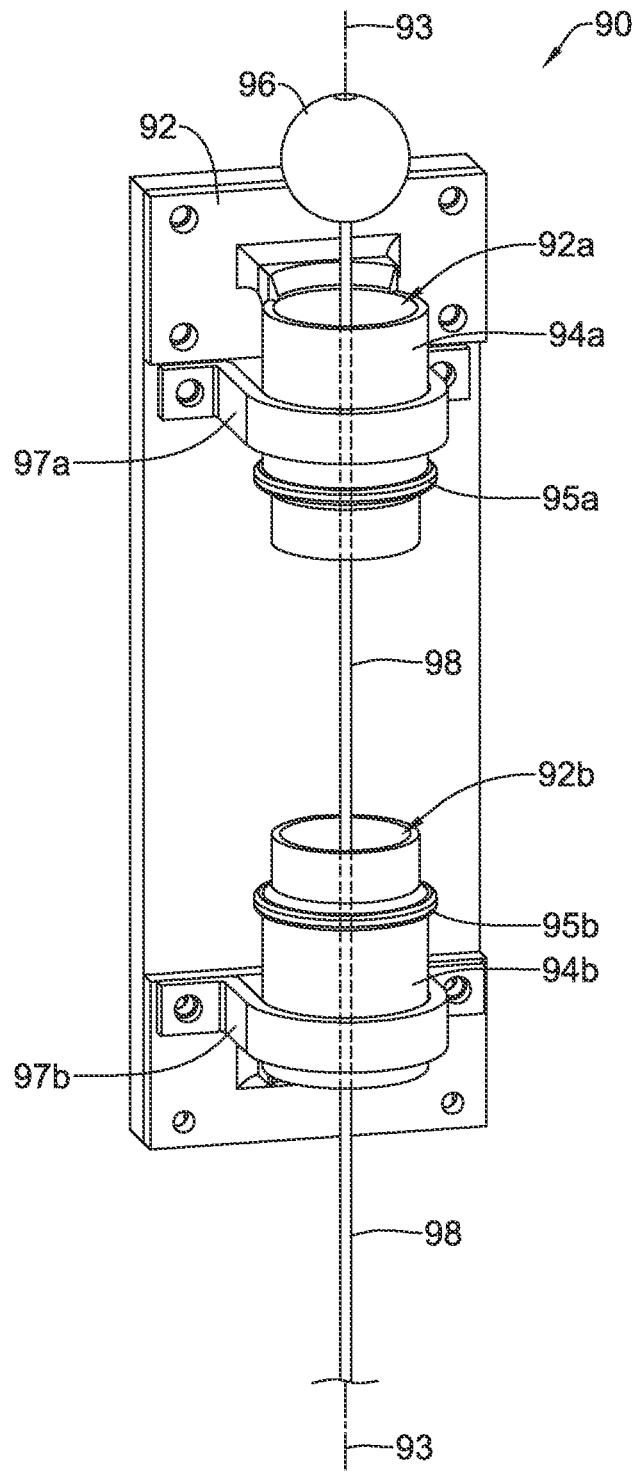
FIG. 17 illustrates an example test fixture.

FIG. 17 illustrates an example bolus force test fixture 90. The test fixture 90 may be utilized to determine the radially outward forces generated by a representative bolus of material passing through the stent 10. As shown in FIG. 17, the test fixture 90 may include a first stent engagement member 94a and a second stent engagement member 94b, each of which are secured to a base 92. The first stent engagement member 94a and the second stent engagement member 94b may be aligned with one another along a longitudinal axis 93. As illustrated in FIG. 17, each of the first stent engagement member 94a and the second stent engagement member 94b may be secured to the base 92 via a first engagement mount or strap 97a (utilized to secure the first stent engagement member 94a to the base 92) and a second engagement mount or strap 97b (utilized to secure the second stent engagement member 94b to the base 92).

Each of the first and the second stent engagement members 94a, 94b may be shaped such that they are designed to engage the first end 21 and the second end 23 of the stent 10 (not shown in FIG. 17, but shown in FIG. 1). For example, each of the first and the second stent engagement members 94a, 94b may include a first protrusion 95a (extending radially outward from the outer surface of the stent engagement member 94a) and a second protrusion 95b (extending radially outward from the outer surface of the stent engagement member 94a). It can be appreciated that the shape of each of the first engagement member 94a and the second engagement member 94b may be designed to mate with the first end 21 and the second end 23 of the stent 10 (not shown in FIG. 17, but shown in FIG. 1). For example, the first protrusion 95a and the second protrusion 95b may each be designed to mate with the enlarged portions 12 of the stent 10.

Additionally, FIG. 17 illustrates that each of the first stent engagement member 94a and the second stent engagement member 94b may include a first lumen 92a and a second lumen 92b, respectively. It can be appreciated that each of the first lumen 92a and the second lumen 92b may be designed (e.g., sized) such that a bolus member 96 may pass therethrough. The bolus member 96 may resemble a spherically shaped ball designed to mimic (e.g., resemble, etc.) a bolus of nutritional material which may pass through the stent 10 (shown in FIG. 1). While FIG. 17 illustrates that bolus member 96 spherically-shaped, other shapes are contemplated to mimic various types of nutritional material passing through the stent 10.

Further, FIG. 17 illustrates that the bolus member 96 may be attached to a pull member 98 which may be designed to pass through the first lumen 92a and the second lumen 92b of the first stent engagement member 94a and the second stent engagement member 94b, respectively. In other words, it can be appreciated that the pull member 98 may be utilized to pull the bolus member 96 along the axis 93 through each of the first stent engagement member 94a and the second stent engagement member 94b, and thus through the valve 16 of a stent 10 mounted to the fixture 90.

Figure 18:
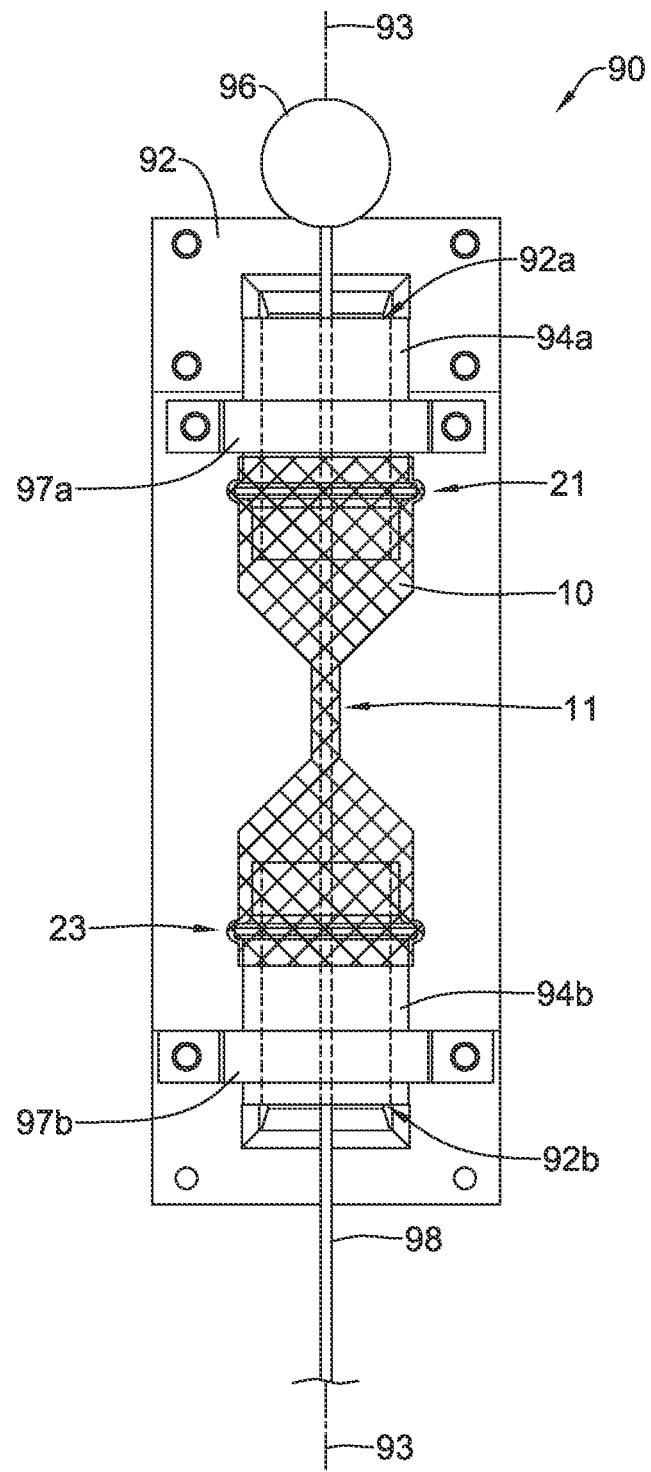
FIG. 18 illustrates an example testing step of the example test fixture shown in FIG. 17.
Figure 19:
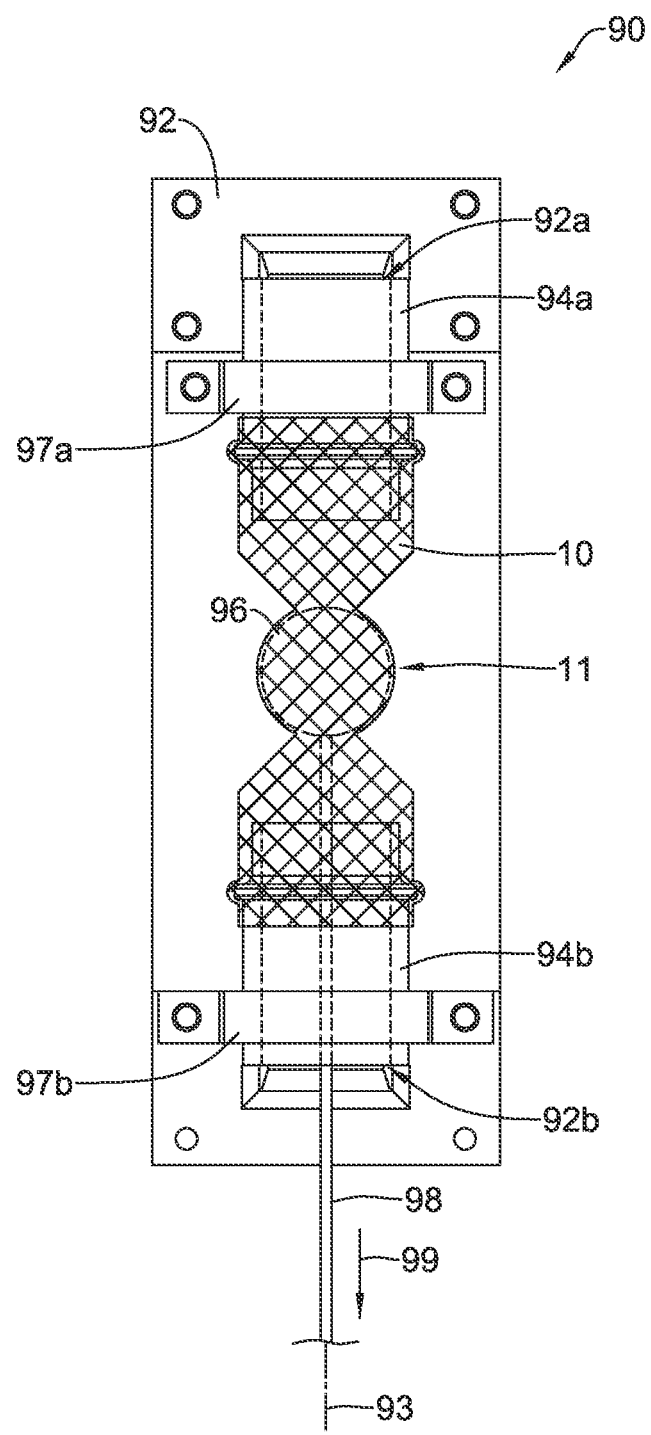
FIG. 19 illustrates another example testing step of the example test fixture shown in FIG. 17.

FIG. 18 and FIG. 19 illustrate the example bolus member 96 being pulled through the stent 10 described above. In particular, FIG. 18 illustrates the first end 21 of the stent 10 mounted to the first engagement member 94a and the second end 23 of the stent 10 mounted to the second engagement member 94b. Further, as described above, FIG. 18 illustrates each of the first engagement strap 97a and a second engagement strap 97b securing the first engagement member 94a and the second engagement member 94b to the base 92.

Additionally, FIG. 18 illustrates the bolus member 96 aligned with the first lumen 94a along the axis 93. Further, the pull member 98 is attached to the bolus member 96 while also extending through the first lumen 92a of the first engagement member 94a, the stent 10 (including the narrowed region 11) and through the second lumen 92b of the second engagement member 94b.

FIG. 19 illustrates the bolus member 96 being pulled through the stent 10. In particular, FIG. 19 illustrates bolus member 96 being pulled through the narrowed region 11 of stent 10. It can be appreciated that to measure the radially outward forces generated by the bolus member 96 as the bolus member 96 is pulled through the stent 10, one or more components of the testing fixture 90 may be attached (e.g., gripped, clamped, supported, etc.) to a force measurement machine (e.g., a tensile testing machine, Instron® machine, etc. It is noted that, for simplicity, the force testing machine is not shown in FIG. 18 or FIG. 19). For example, in some instances, the base 92 may be secured to one portion of the force testing machine while the pull member 98 may be attached to another portion of the force testing machine.

Further, the force testing machine may be designed to "pull" the pull member 98 (which is attached to the bolus member 96) through the stent 10, as indicated by the arrow 99 in FIG. 19. As the pull member 98 pulls the bolus member 96 through the stent 10 (e.g., through the narrowed region 11 of stent 10 as shown in FIG. 19), the force testing machine may continuously record the radially outward forces generated by the bolus member 96 as it advances through the stent 10, as a function of the axial force measured. It can be appreciated that the speed with which the bolus member 96 is pulled through the stent 10 may be varied to better understand how the stent reacts (e.g., the force variations placed upon the stent 10) as the bolus member 96 passes through the stent 10 at varying speeds.

In some instances, the test methodology described above has shown that the radially outward forces generated by the bolus member 96 having a diameter of 15 mm may be in the range of between 2.40 N to 4.70 N as the bolus member 96 is pulled through the stent 10 at a speed of 5 mm/s, in the range of between 2.20 N to 3.40 N as the bolus member 96 is pulled through the stent 10 at a speed of 7 mm/s, in the range of between 2.20 N to 3.30 N as the bolus member 96 is pulled through the stent 10 at a speed of 10 mm/s, in the range of between 2.00 N to 3.30 N as the bolus member 96 is pulled through the stent 10 at a speed of 12 mm/s, and in the range of between 2.0 N to 3.30 N as the bolus member 96 is pulled through the stent 10 at a speed of 15 mm/s, for example. Thus, in such an instance, the filaments 14 should exert a radially inward compressive force of less than 2.0 N, less than 1.5 N, or less than 1.0 N in a nominally deployed state to ensure that the valve 16 will open sufficiently to permit a bolus of material to pass through the valve 16.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An expandable stent, comprising:
   a tubular scaffold formed of one or more interwoven filaments, the tubular scaffold defining a lumen and including an inner surface and an outer surface; and
   a flexible valve extending radially inward from the inner surface of the tubular scaffold;
   wherein the one or more filaments of the scaffold are configured to shift the flexible valve from an open configuration to a closed configuration;
   wherein the one or more filaments are biased radially inward to hold the flexible valve in the closed configuration while in a nominally deployed state.

2. The stent of claim 1, wherein the valve is configured to shift from the closed configuration to the open configuration due to a peristaltic force applied to the tubular scaffold.

3. The stent of claim 1, wherein the valve includes a valve opening extending therethrough, and wherein the valve opening is ovular-shaped in the open configuration.

4. The stent of claim 1, where the tubular scaffold includes a narrowed region and the valve is positioned in the narrowed region.

5. The stent of claim 1, wherein the one or more filaments of the scaffold are configured to radially expand to shift the valve from the closed configuration to the open configuration when subjected to a radial expansion force of 0.200 N/cm$^2$ or greater.

6. The stent of claim 1, wherein the one or more filaments of the scaffold are configured to radially expand to shift the valve from the closed configuration to the open configuration when subjected to a radial expansion force of 0.800 N/cm$^2$ or greater.

7. The stent of claim 1, further comprising a coating disposed along the one or more filaments, and wherein the valve is formed from a portion of the coating.

8. The stent of claim 7, wherein the tubular scaffold has a first end, a second end, and a length extending therebetween, wherein the coating extends along an entirety of the length of the tubular scaffold.

9. The stent of claim 7, wherein the coating extends along only the inner surface of the tubular scaffold.

10. The stent of claim 7, wherein the coating extends along both the inner and outer surfaces of the tubular scaffold.

11. The stent of claim 1, wherein the valve is an annular member extending continuously around the lumen of the tubular scaffold.

12. The stent of claim 1, wherein the tubular scaffold has an hourglass shape with a narrowed waist in the closed configuration, wherein the valve is disposed within the narrowed waist.

13. The stent of claim 12, wherein the one or more interwoven filaments are heat set in the hourglass shape.

14. The stent of claim 1, wherein the one or more interwoven filaments form one or more flanges defining regions of increased diameter.

15. An expandable stent, comprising:
a tubular scaffold formed of a plurality of interwoven filaments, the tubular scaffold including a first end, a second end and a lumen extending therethrough; and
a flexible valve defined within the lumen;
wherein the plurality of interwoven filaments are configured to move the flexible valve from an open configuration to a closed configuration;
wherein the plurality of interwoven filaments apply a radially compressive force on the valve to bias the valve in the closed configuration while the stent is in a nominally deployed state.

16. The stent of claim 15, wherein the tubular scaffold includes a narrowed region positioned between the first end and the second end, wherein the valve is formed in the narrowed region.

17. The stent of claim 15, wherein the radially compressive force is less than or equal to 0.800 N/cm2.

18. The stent of claim 15, further comprising a coating disposed along the plurality of filaments, and wherein the valve is formed from a portion of the coating.

19. An expandable stent, comprising:
a tubular scaffold having a first end, a second end, and defining a lumen extending therebetween; and
a flexible valve extending radially inward from the inner surface of the tubular scaffold;
wherein the tubular scaffold is configured to shift the flexible valve from an open configuration to a closed configuration;
wherein the tubular scaffold is biased to hold the valve in the closed configuration while in a nominally deployed state.

20. The stent of claim 19, wherein the tubular scaffold includes a narrowed region positioned between the first and second ends, and wherein the valve is positioned in the narrowed region.

* * * * *